(12) United States Patent
Cohen et al.

(10) Patent No.: US 8,845,096 B1
(45) Date of Patent: Sep. 30, 2014

(54) VISION THERAPY SYSTEM

(76) Inventors: Allen H. Cohen, New York, NY (US);
Rodney K. Bortel, Gold Canyon, AZ (US)

(*) Notice: Subject to any disclaimer, the term of this patent is extended or adjusted under 35 U.S.C. 154(b) by 167 days.

(21) Appl. No.: 13/316,013

(22) Filed: Dec. 9, 2011

Related U.S. Application Data

(60) Provisional application No. 61/421,429, filed on Dec. 9, 2010.

(51) Int. Cl.
*A61B 3/00* (2006.01)

(52) U.S. Cl.
USPC .......................................... 351/203; 351/246

(58) Field of Classification Search
USPC ............ 351/200, 203, 223, 239, 246; 601/37
See application file for complete search history.

(56) References Cited

U.S. PATENT DOCUMENTS

2008/0278682 A1* 11/2008 Huxlin et al. ................. 351/203

* cited by examiner

*Primary Examiner* — Mahidere Sahle
(74) *Attorney, Agent, or Firm* — Schmeiser, Olsen & Watts LLP

(57) ABSTRACT

A visual therapy system is provided that includes a computer, a projector, a display, and input devices, including a head sensor remote, a sensor bar, a balance board, hand controlled remote, and a head sensor. The system uses an interactive interface and blue tooth software that combines remotes, an interactive balance board and infra-red head sensors. The system provides specialized therapy modules which may be based on the concept of Top Down Processing and may be designed to enhance ocular motor control, visuomotor and binocular performance while integrating vision, auditory, proprioception, balance and visuomotor control.

20 Claims, 9 Drawing Sheets

VISION THERAPY SYSTEM

CROSS REFERENCE TO RELATED APPLICATION[S]

This application claims priority to U.S. Provisional Patent Application entitled Vision Therapy System," Ser. No. 61/421,429, filed Dec. 9, 2010, the disclosure of which is hereby incorporated entirely herein by reference.

BACKGROUND OF THE INVENTION

1. Technical Field

This invention relates generally to a vision therapy system and more particularly to an interactive vision therapy system.

2. State of the Art

There exist instances where people suffer from neuro-vision processing deficits. These deficits include deficits in the visual processing skills necessary for "Top Down" information processing (magnocellular and dorsal stream). Deficits in these skills are commonly associated with neurological insult, acquired brain injury, post trauma vision syndrome, Defuse Axonal Injury (DAI) and stroke, as well as the brain filtering problems frequently encountered in children and adults with visually related learning problems.

When a person suffers from these neuro-vision processing deficits, often they must go through some type of visual therapy. The ultimate goal of visual therapy is to enhance the speed and efficiency of visual information processing in order to react to an input, which is usually sensory information from our environment. Since ocular fixation and eye movement is the aiming "device" for the visual system, the ability to accurately control the eyes with the least amount of energy is an extremely important skill to develop. One critical component of ocular motor control is the response speed of the extra-ocular neuro-muscle system. It is important to be able to move the eye system without support or interference from slower and grosser muscle systems such as the head and body.

While conventional systems have been employed in attempts to provide this vision therapy, these conventional systems have their drawbacks. They do not provide well organized and repetitive procedures, which are crucial to enhance of synaptic transmission (motor planning) in order to improve a patient's neurological control of the motor system. Further, these systems are lacking in their ability to provide quality and timely feedback to the patient, which harms the overall effectiveness of the conventional systems.

Accordingly, there is a need in the field of vision therapy systems, for an improved system that addresses at least the previously stated drawbacks of existing systems.

DISCLOSURE OF THE INVENTION

The present invention relates to a state of the art vision therapy system, which uses an interactive interface and blue tooth software that combines remotes, an interactive balance board and infra-red head sensors. The system provides specialized therapy modules which may be based on the concept of Top Down Processing and may be designed to enhance ocular motor control, visuomotor and binocular performance while integrating vision, auditory, proprioception, balance and visuomotor control.

Although there are currently many vision therapy procedures available that adequately normalize the neuro-muscular control of ocular motor, accommodation and binocular performance, visual therapy procedures to enhance the integration of this visual input with balance, auditory and visuomotor performance at a cortical level are severely lacking.

The system represents an interactive, integrative, real space vision therapy system specifically designed to address the visual processing problems commonly experienced by patients with neurological insult, acquired brain injury, post trauma vision syndrome, Defuse Axonal Injury (DAI) and stroke, as well as the brain filtering problems frequently encountered in children with visually related learning problems.

The ultimate goal of visual therapy is to enhance the speed and efficiency of visual information processing in order to react to an input, which is usually sensory information from our environment. Since ocular fixation and eye movement is the aiming "device" for the visual system, the ability to accurately control the eyes with the least amount of energy is an extremely important skill to develop. One critical component of ocular motor control is the response speed of the extra-ocular neuro-muscle system. It is important to be able to move the eye system without support or interference from slower and grosser muscle systems such as the head and body. Since the neurological control of the motor system is the outcome of synaptic transmission (motor planning), this skill can be enhanced through well-organized and repetitive procedures. The way the brain "learns" is by responding to multi-sensory alerts with a controlled response to these alerts and processing feedback as to whether the response is correct or incorrect. The effectiveness of a vision therapy procedure is not determined by how physically hard it is but by how much reinforced feedback it presents to the patient It is understood that efficient visual information processing and performance is dependent upon the integrity of sensory input, speed of neurological integration of multisensory input and efficiency of motor output, a form of Top Down processing.

The system provides specialized therapy modules designed to enhance ocular motor, visuomotor and binocular performance while integrating vision, auditory, proprioception, balance and visuomotor control. Aspects of the invention include a visual therapy system that comprises a remote, an integrative balance board and an infra-red head sensor to create an interactive interface, wherein the interactive interface provides uniquely powerful procedures designed to significantly enhance deficits in visual processing skills in real space. Neuroscience has demonstrated that repetition, multisensory feedback, and active participation in sensory motor tasks are essential for affecting synaptic and neuroplasticity changes. These are the changes that translate into increased speed of information processing and performance.

The interactive head sensor of the system provides a feedback alert through the use of vibration, wherein the vibration felt in the hand sensor remote allows the patient to know when he or she is using too much unfruitful motor response (head or body) to visually seek out the target. When the brain has recalibrated the neurological control of the ocular motor system and the patient realigns their head, the vibration ceases, thus providing positive feedback. This graded alert, combined with the success of the task being repeated over and over again provides a powerful conditioning procedure for neuroplasticity.

The interactive balance board enhances the patient's ability to adjust his or her internal proprioceptive sensitivity to the sensory demand. The patient modulates and re-calibrates his or her proprioceptive control of his or her motor system as a response to the visual and auditory tones provided by the interaction of the system software and interactive balance board.

A particular embodiment of the present invention includes a method of using a vision therapy system having a computer operating the system, a projector projecting visual graphics, a display for displaying the projection, and input devices for providing interaction by the user with the system. The method comprises initiating first phase of a vision therapy of enhancing the stability of the visual input system, wherein enhancing the stability of the visual input system comprises performing at least one of a first phase visual motor enhancer (VME) module vision therapy, a first phase ocular vestibular integrator (OVI) module vision therapy, a first phase dynamic ocular motor processing (DOMP) module vision therapy and a first phase visuomotor integrator (VMI) module vision therapy; initiating second phase of the vision therapy of developing fusional sustenance; and initiating third phase of the vision therapy of developing speed of visual information processing and stability of visuomotor performance, wherein the developing speed of visual information processing and stability of visuomotor performance comprises performing at least one of a third phase VME module vision therapy, a third phase OVI module vision therapy, a third phase DOMP module vision therapy and a third phase VMI module vision therapy.

In some embodiments, enhancing the stability of the visual input system comprises performing a first phase fixation anomalies (FA) module vision therapy. Further, in some embodiments, developing speed of visual information processing and stability of visuomotor performance comprises performing a third phase FA module vision therapy.

In some embodiments, the method may further comprises scoring a performance of a user in each phase of the vision therapy; and adjusting the vision therapy of each phase in response to reaching predetermined scoring levels.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

As discussed above, embodiments of the present invention relate to a state of the art visual therapy system, which uses an interactive interface and blue tooth software that combines remotes, an interactive balance board and infra-red head sensors. The system provides specialized therapy modules which may be based on the concept of Top Down Processing and may be designed to enhance ocular motor control, visuomotor and binocular performance while integrating vision, auditory, proprioception, balance and visuomotor control.

Figure 1:
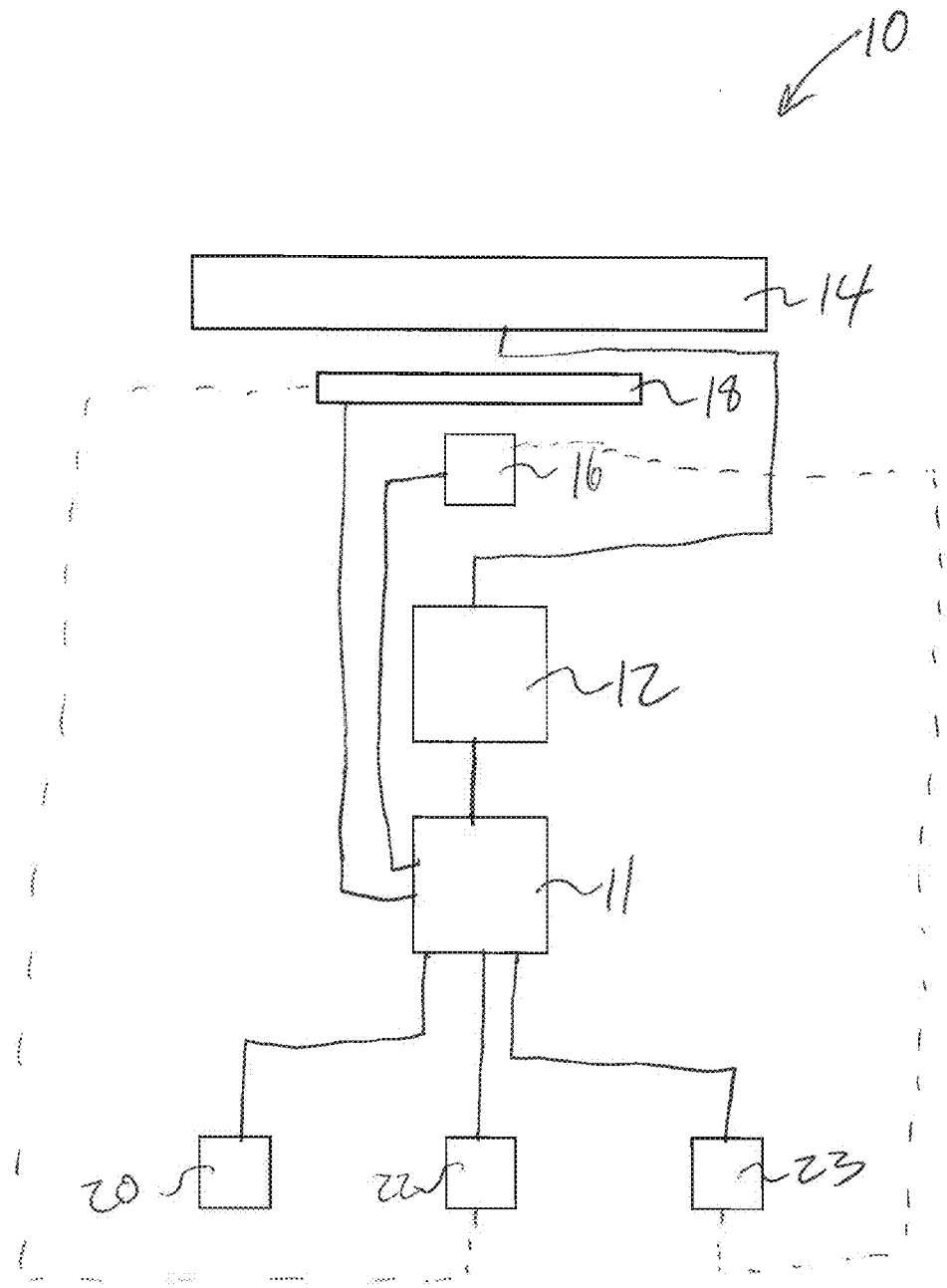
FIG. 1 is a diagrammatic view of a vision therapy system.
Figure 2:
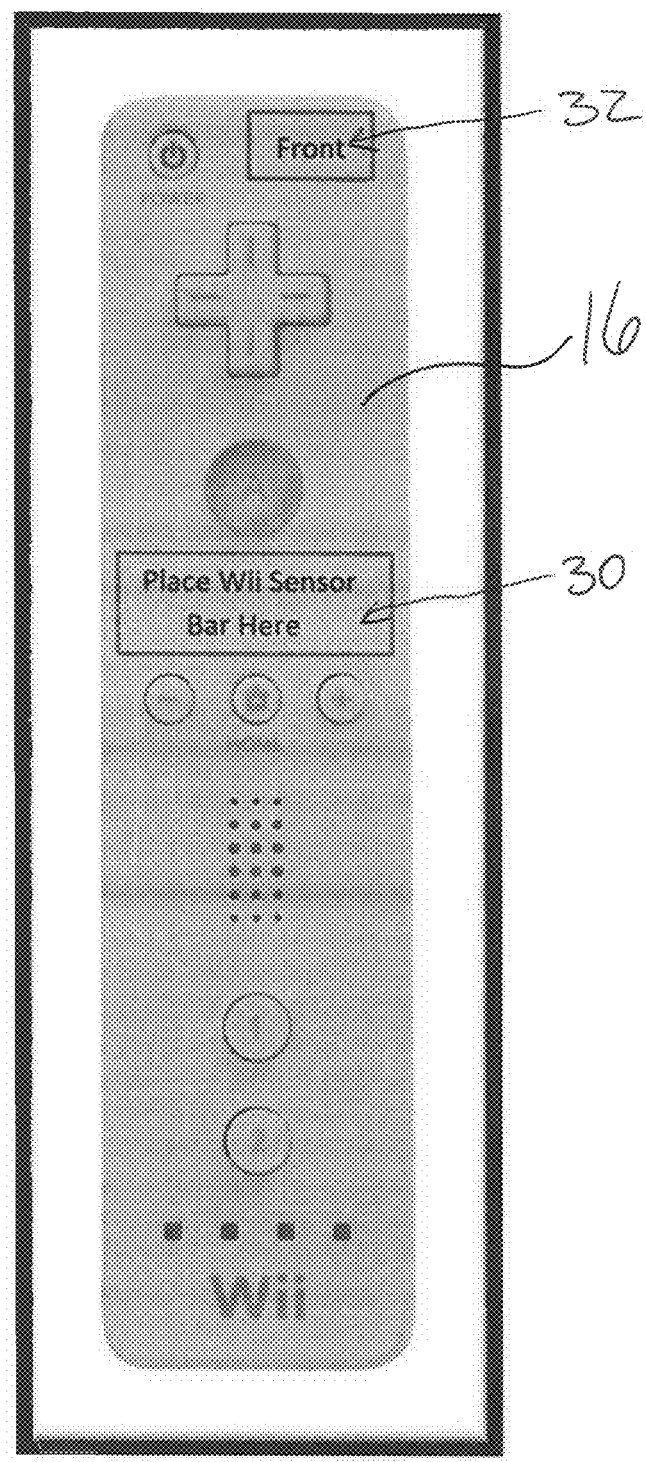
FIG. 2 is a top view of a head sensor remote of a vision therapy system.

As shown in FIG. 1, embodiments of a visual therapy system 10 include a computer 11, a projector 12, a display 14, and input devices, comprising a head sensor remote 16, a sensor bar 18, a balance board 20, hand controlled remote 22, and a head sensor 23. These components of system 10 allows a user to operate the system 10 to perform visual therapy, such as specialized therapy modules provided by a software product installed on memory of the computer 11.

In particular embodiments, the projector 12 is placed in line with the center of a projection screen or display 14, and further may be placed 10 to 15 feet from the projection screen, and mounted high enough so that the projection will be above the users head. The projection screen allows the projector 12 to project a user interface onto the display 14.

The software program is installed on memory of the computer 12. The processor of the computer 12 processes information regarding the software program in response to activation of the software program, such as by using a mouse interface to select and activate and executable file corresponding to the software product of embodiments of the system 10. Once the software product is activated and operational on the computer 12, the software product allows a user to perform visual therapy by use of several user input devices that are in communication with one of either another input device or the computer 12. Use of the software product may be restricted by use of a HASP device, such as, but not limited to a USB HASP dongle.

The system 10 may further include a Bluetooth device connected to the computer 12 for communication with particular input devices. The Bluetooth device may require a driver wherein the driver allows the computer to recognize the Bluetooth device and further allows the processor to process information received from the Bluetooth device for use with the software program.

Figure 3:
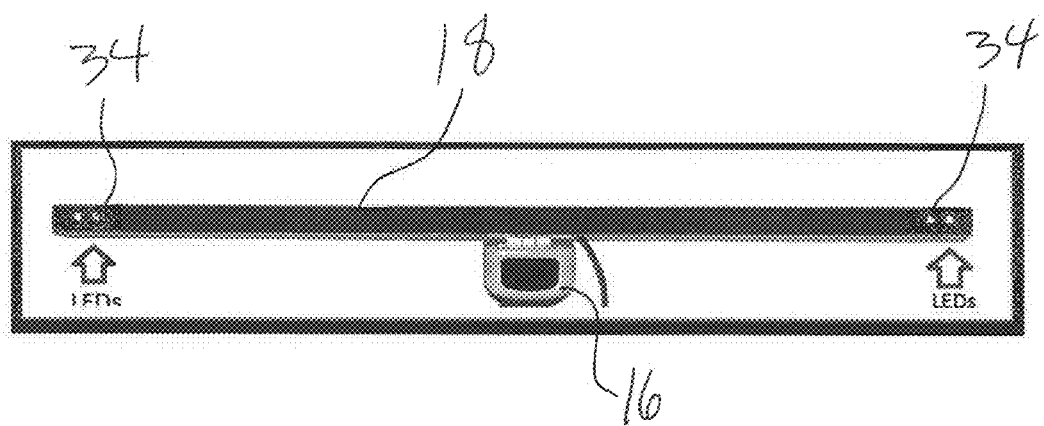
FIG. 3 is a front view of a sensor bar and a head sensor remote of a vision therapy system.
Figure 4:
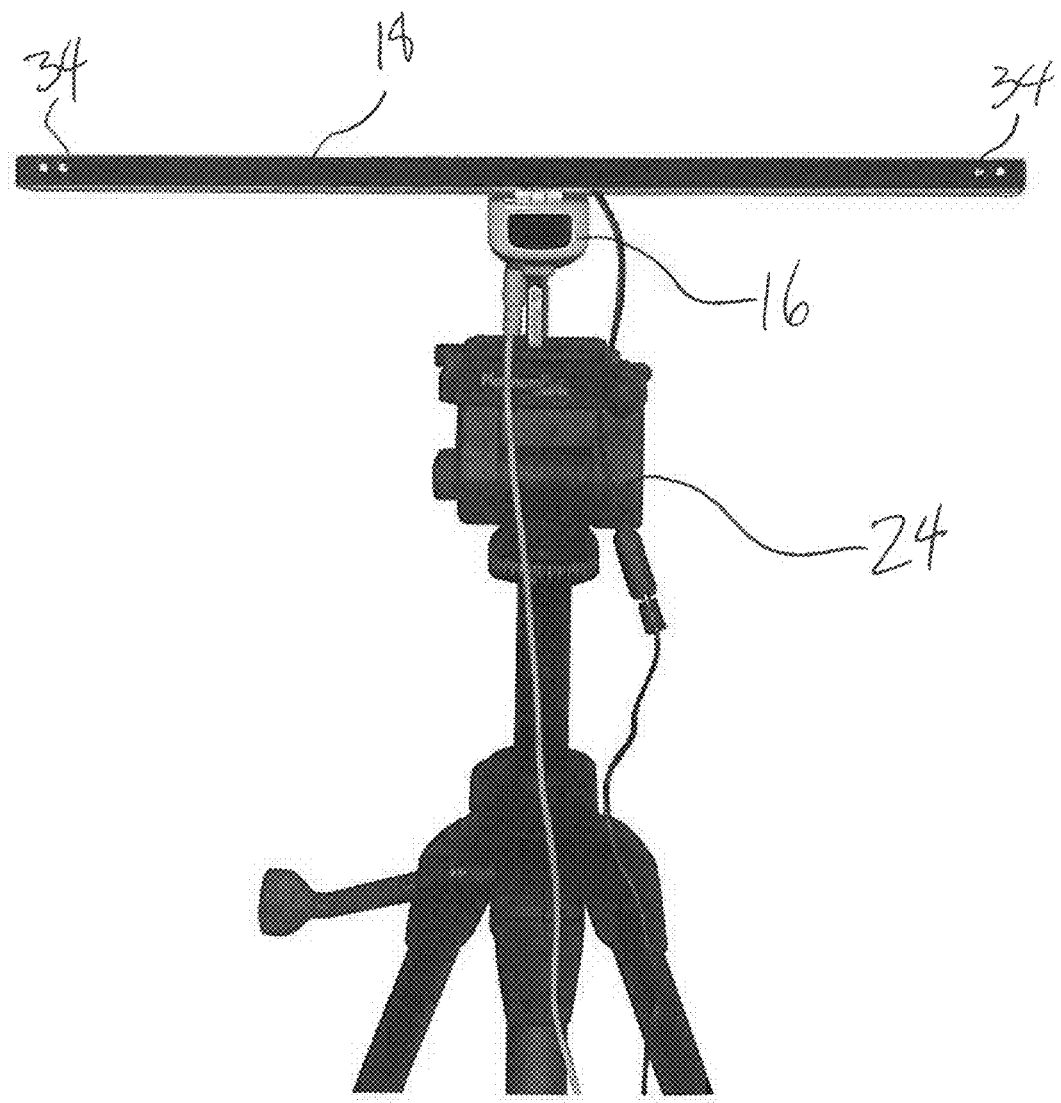
FIG. 4 is a front view of a sensor bar and a head sensor remote removably secured to a base support of a vision therapy system.

Referring further to FIGS. 2-5 and according to particular embodiments of the present invention, the head sensor remote 16 may be coupled to the sensor bar 18, wherein the sensor bar 18 is transverse to the remote 16, as shown in FIG. 3. For example, and without limitation, the sensor bar 18 may be coupled to the head sensor remote 16 by use of an adhesive tape. The location of the sensor bar 18 on the head sensor remote 16 may be between the "A" and the "Home" buttons as shown by area 30 on the head sensor remote 16. The two LEDs 34 on each end of the Sensor Bar face toward the front of the remote 16 indicated by area 32, as shown in FIGS. 3 and 4.

Figure 5:
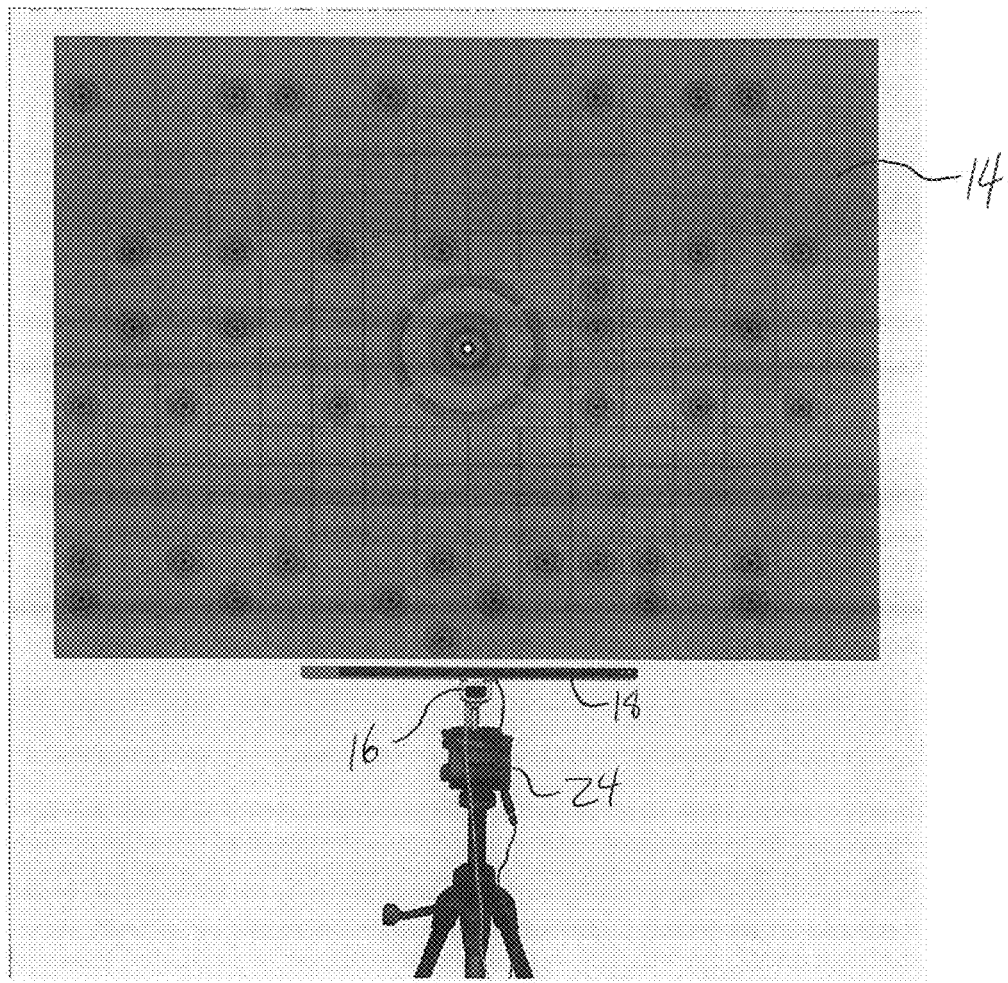
FIG. 5 is a front view of a sensor bar and a head sensor remote removably secured to a base support placed adjacent a display of a vision therapy system.

The system may further comprise a head sensor remote base 24, as shown in FIG. 4. Base 24 may be in the form of a tripod as shown in FIG. 4, but it is contemplated that any base may be used to support and hold the head sensor remote 16 and the sensor bar 18 in a stationary position and located properly with respect to the user interface on the display 14. The base 24 may be positioned to line up with the center of the projected area of the display 14, as shown in FIG. 5. The height of the base may then be adjusted so the top of the Sensor Bar is just below the projected image. Base 24 is substantially level and parallel to the ground, wherein the head sensor remote 16 and the sensor bar 18 are also maintained substantially parallel to the ground in response to releaseably attaching the head sensor remote 16 to the base. The front of the head sensor remote 16 should be pointing in a direction transverse to the display 14, as shown in FIG. 5.

Figure 6:
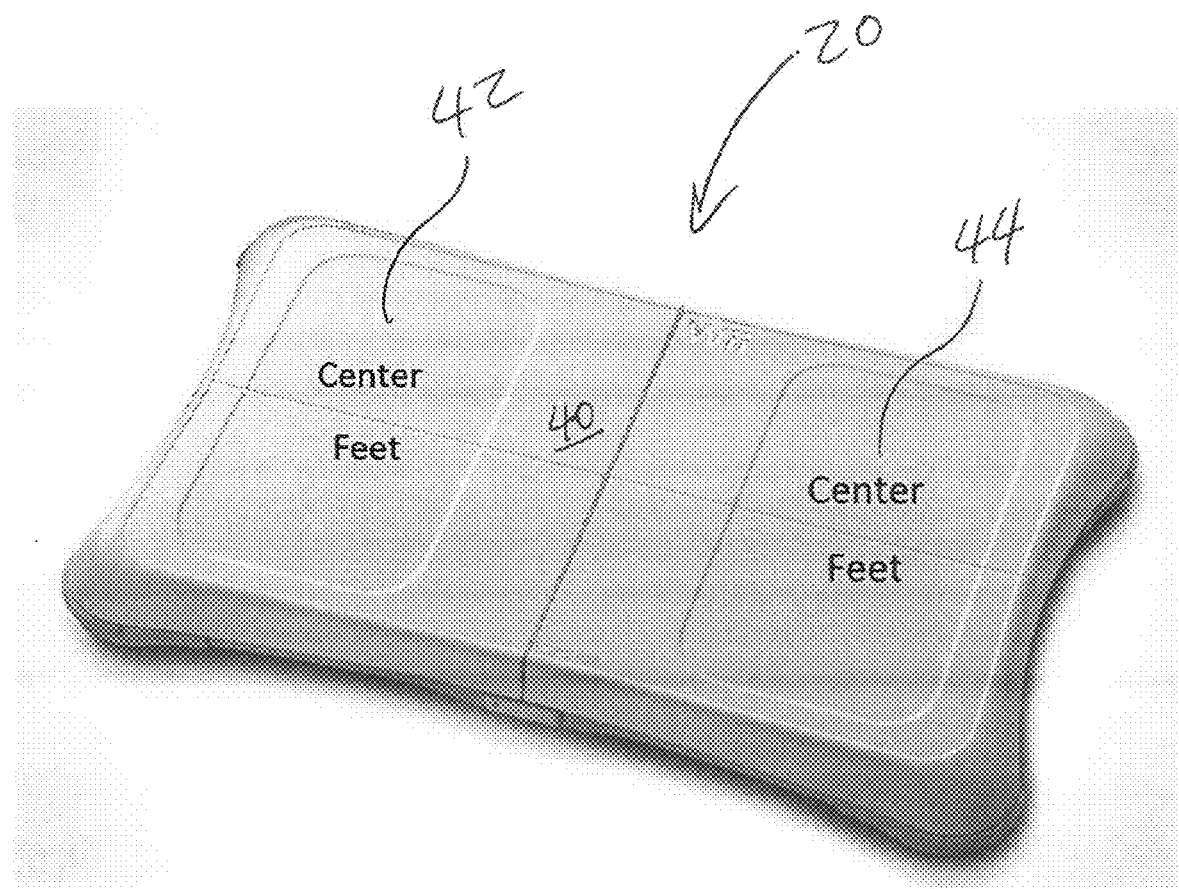
FIG. 6 is a perspective view of a balance board of a vision therapy system

Referring to FIG. 6, the balance board 20 of the system 10 is programmed to respond to changes in a user's balance. Embodiments of the system 10 include the balance board 20 placed such that it is centered with the display 14. A user stands on the balance board 20 with his or her feet centered in the two footpad areas 42 and 44 located on a top surface 40 of the balance board 20. In operation, the user's feet are placed and substantially equally centered both side to side and front to back. The user's feet must be placed flat on the balance board 20 and therefore it is contemplated that the user will remove his or her shoes while using the balance board 20. Balance board 20 is positioned such that a user standing on balance board 20 and looking straight ahead will be looking at the center of display 14. Balance board 20 is used to provide feedback to the user regarding the amount of body movement used in performing tasks.

Figure 7:
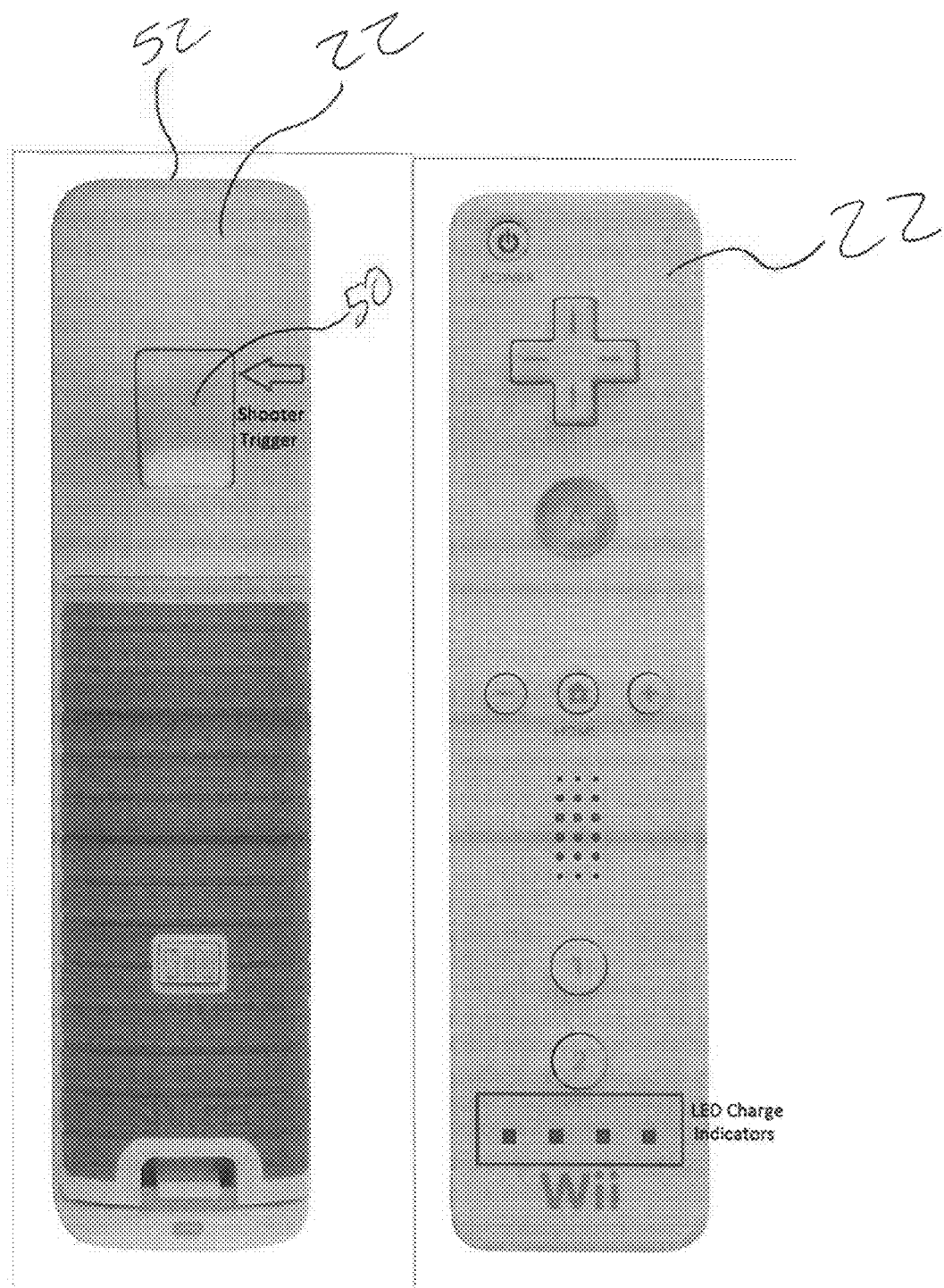
FIG. 7 is a view of a hand controlled remote of a vision therapy system.

Referring to FIG. 7, the hand controlled remote 22 of the system 10 is a user's primary tool for interacting with the system 10. In particular embodiments, the only button on the hand controlled remote 22 that is used is the trigger 50. The hand controlled remote 22 allows a user to "shoot" objects or targets on the display, or in other words to point an indicator that is represented by, but not limited to, a "Red Dot" on the display 14 in response to pointing the front end 52 of the hand controlled remote 22 at the display 14, wherein the sensor bar 18 determines the location of the indicator on the display 14 in response to receiving a signal from the hand controlled remote 22. It allows for up, down, left, and right hand movements. Visual therapy procedures are performed by having the user visually locate targets in display 14, and then use the hand-controlled remote 22 to position the Red Dot in a selected position with respect to the target. In some procedures the user shoots the target using trigger 50.

Figure 8:
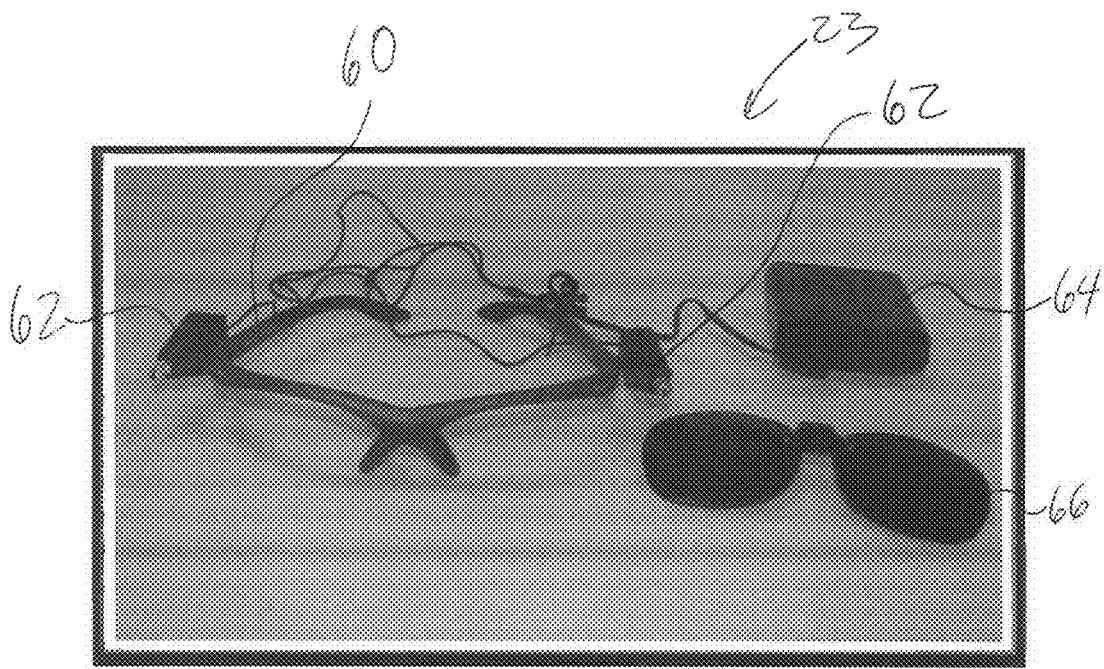
FIG. 8 is a perspective view of a head sensor of a vision therapy system.
Figure 9:
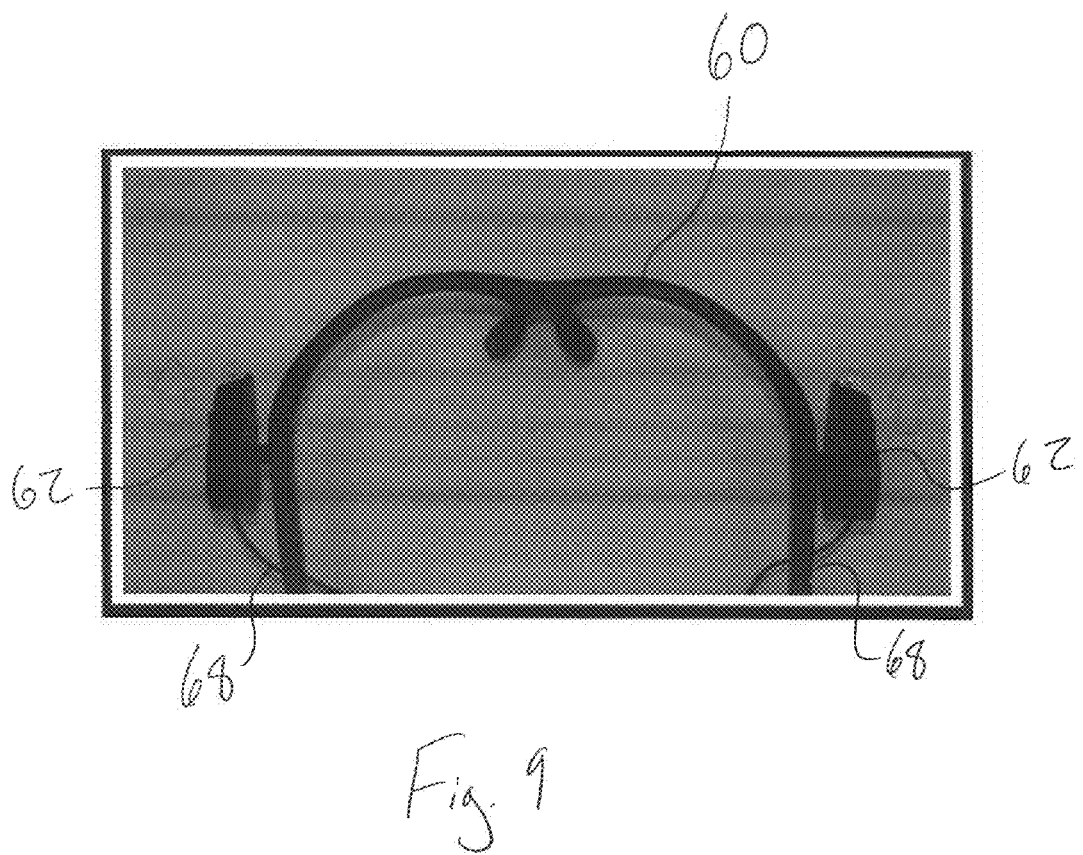
FIG. 9 is a top view of a head sensor of a vision therapy system.

Referring to FIGS. 8 and 9, the system 10 further includes a head sensor 23 for alerting a user if he or she moves his or her head while performing the visual therapy procedures. The head sensor 23 includes sensor glasses frames 60 with two infrared LED emitters 62 on opposing sides of the frames 60 and a power source 64. The LED emitters 62 face forward in a direction aligned with ear rests 68 of the frames 60. The head sensor 23 also includes a pair of red/blue clip-on lenses 66 which are used with the red/blue and stereo visual therapy procedures.

The ultimate goal of visual therapy is to enhance the speed and efficiency of visual information processing in order to react to an input, which is usually sensory information from our environment. Since ocular fixation and eye movement is the aiming "device" for the visual system, the ability to accurately control the eyes with the least amount of energy is an extremely important skill to develop. One critical component of ocular motor control is the response speed of the extraocular-neuromuscle system. It is important to be able to move the eye system without support or interference from slower and grosser muscle systems such as the head and body. Since the neurological control of the motor system is the outcome of synaptic transmission (motor planning), this skill can be enhanced through well organized and repetitive procedures. The way the brain "learns" is by responding to multi-sensory alerts with a controlled response to these alerts and processing feedback when the response is correct or incorrect. The effectiveness of a vision therapy procedure is not determined by how physically hard it is but by how much reinforced feedback it presents to the patient.

The interactive head sensor 23 and balance board 20 of the system 10 accomplish this goal by providing a feedback alert in the form of vibration felt in the hand controlled remote 22. This allows the user to know when he or she is using too much unfruitful motor response (head or body) to visually seek out the target. When the brain has recalibrated the neurological control of the ocular motor system and the user realigns his or her head or body, the vibration ceases, thus providing positive feedback. This graded alert, combined with the success of the task being repeated over and over again provides a powerful conditioning procedure for neuroplasticity.

Accordingly, the purpose of the head sensor 23 and balance board 20 is not to prevent the user from moving his or her head or body but to alert him or her when he or she is moving his or her head or body, thus adding a multisensory feedback component to the visual therapy procedure.

It is contemplated that embodiments of the present invention may include various methods of employing visual therapy. For example, and without limitation, embodiments may include visual therapy modules that are performed using the system 10. These modules may include, without limitation, a visual motor enhancer module, an ocular vestibular integrator module, a dynamic ocular motor processing module, a visuomotor integrator module and a fixation anomalies module. Each module may be performed independent of the other modules and users may alternate between any number of provided modules dependent upon the needed visual therapy. The following are more detailed descriptions of the modules listed above.

1. Visual Motor Enhancer (VME) Module

The VME Module includes a virtual rotator with several options that allows a user to control speed and/or direction of rotation of a target shown in display 14, selection of targets, randomization of target presentation, jump saccadics, as well as auto or manual mode control. There are 4 levels that use the full interactive ability of the system 10 by allowing for the addition of the balance board 20 and/or the head sensor 23. Auditory feedback from hand controlled remote 22 serves to develop and enhance ocular fixation, pursuits, and rotations while integrating balance and visuomotor control.

Generally, a method of performing a visual motor enhancer module vision therapy by use of a vision therapy system comprises the steps of providing a target on a display in response to running of a software product; rotating the target at a particular speed; locating a hand controlled remote indicator on the target on the display; shooting the target in response to depression of a trigger of the hand controlled remote; and providing feedback as to whether head and/or body motion is detected. Additional method steps are provided in greater detail below.

2. Ocular Vestibular Integrator (OVI) Module

This treatment module is designed to enhance Top Down guidance of ocular motor, balance and graphomotor performance. The OVI Module projects bull's eyes in the periphery of the screen that randomly light up when a user accurately shoots them out with the hand controlled remote 22. A user may change the number of targets presented, the number of bull's eyes per quadrant (important for treatment of visual field defects), visual distracters in the periphery, size of fixation charts and type of targets in the fixation charts. There are six levels that use the full interactive ability of the system 10 by allowing for the addition of the balance board 20 and head sensor 23.

Additionally, this module incorporates two additional features, an auditory command in addition to visual clues designed to help initiate a saccadic fixation. Also available are red/blue chart targets which require fusion, thus resulting in stereopsis. The OVI module enhances the processing of auditory, balance and stable binocular vision inputs, which is important in establishing a more normal Vestibular Ocular Reflex (VOR) addressing symptoms of dizziness and disequilibrium.

Generally a method of performing an ocular vestibular integrator module vision therapy by use of a vision therapy system comprises the steps providing a target on a display in response to running of a software product; locating the target in a peripheral view of a user defined by the user directing the user's eyes straight at the display; directing a user to locate the target with his eyes; locating a hand controlled remote indicator on the target on the display; shooting the target in response to depression of a trigger of the hand controlled remote; and sounding an auditory alert that the target has been shot. Additional method steps are provided in greater detail below.

3. Dynamic Ocular Motor Processing (DOMP) Module

This module is effective for enhancing "Top Down" speed of visual processing. This module presents procedures that require a higher level of visual processing than OVI Module due to the addition of contour interaction (magnocellular) and associated random clues for ocular fixation (parvocellular), spatial relations, visual sequencing and visual organization. There are five levels that use the full interactive ability of the system 10 by allowing for the addition of the balance board 20, head sensor 23, hand controlled remote 22, and auditory feedback. A user may control the type of and number of background targets, the number of stimuli for guiding fixation and anti-suppression as well as stereopsis targets in level 5 and 6. These procedures are designed to enhance stimulus generated saccadic fixation, visual scanning, visuomotor control, visual spatial processing speed and visual sequencing as well as dynamic sensory binocular fusion.

Generally, a method of performing a dynamic ocular motor processing module vision therapy by use of a vision therapy system comprises the steps of providing a plurality of targets on a display in response to running of a software product; establishing parameters of which targets of the plurality of targets the user is to locate and what order to locate the targets; locating a hand controlled remote indicator on the target on the display; shooting the target in response to depression of a trigger of the hand controlled remote; repeating the locating and shooting steps for each target established by the parameters until the user has shot once at each target; and sounding an auditory alert whether the target has or has not been shot in response to each instance a user shoots at a target. Additional method steps are provided in greater detail below.

4. Visuomotor Integrator (VMI) Module

This treatment module presents procedures designed to enhance ocular motor control, visually guided graphomotor performance and visual spatial processing. There are five levels that use the full interactive ability of the system 10 by allowing for the addition of the balance board 20 and head sensor 23. In Level 1 a user may turn off or on a visual stimulus to guide pursuits and visually guided graphomotor performance. The doctor may add red/blue targets for anti-suppression control. Levels 2 allows a user to enhance visuomotor performance by instructing the user push a golf cart around obstacles on a golf course using the indicator produced in response to operation of the hand controlled remote 22. Level 3 allows a user to increase the level of visuomotor control by automatically following a golf cart that randomly changes speeds and direction. Level 4 adds a higher level of Top Down processing to visuomotor performance by adding tasks that require visual memory while visually guiding the hand controlled remote indicator to match a coded stimulus.

Generally, a method of performing a visuomotor integrator module vision therapy by use of a vision therapy system comprises the steps of providing a first target, a second target and a line connecting the first target and second target on a display in response to running of a software product; locating a hand controlled remote indicator on the first target on the display; locating a user's eyes on the first target in response to input from a head sensor; directing the hand controlled remote indicator along the line from the first target to the second target while synchronously following the hand controlled remote indicator along the line with user's eyes; and sounding an auditory alert in response to the eye/eyes and hand losing synchronization. Additional method steps are provided in greater detail below.

5. Fixation Anomalies (FA) Module

The Fixation Anomalies module contains three interactive therapy procedures designed to enhance fixation anomalies associated with intrusion fixation, nystagmoid fixation, eccentric fixation and associated crowding phenomenon.

The three procedures progressively increase the demand for neural re-calibration of retino-motor and retino-spatial processing. The Fixation Anomalies module adds the therapeutic power of the auditory alert tones provided by the hand controlled remote 22, head sensor 23 and the balance board 20 to enhance the effects of biofeedback through top down processing.

Generally, a method of performing a fixation anomalies module vision therapy by use of a vision therapy system comprises the steps of randomly providing a plurality of marked targets and a plurality of unmarked targets on a display in response to running of a software product; locating one marked target of the plurality of marked targets; locating a hand controlled remote indicator on the one marked target on the display; shooting the target in response to depression of a trigger of the hand controlled remote; maintaining the hand controlled remote indicator steady on the one marked target for a predetermined period of time; and sounding an auditory alert in response to the hand controlled remote indicator moving off of the one marked target. Additional method steps are provided in greater detail below.

Sequencing therapy is contemplated by the present invention because an optometric visual therapy generally progresses in stages with the emphasis of each stage dependent of the diagnosed visual problems. The goals of optometric visual therapy (neuro-optometry and behavioral optometry) can be divided into four areas:

1. Eliminate and manage diagnosed ocular health problems.
2. Eliminate/resolve optical problems.
3. Eliminate/resolve/enhance ocular motor, accommodative, binocular dysfunctions.
4. Enhance speed of visual and visuomotor processing (Top Down Processing).

The vision therapy system of the present invention is specifically designed to address the visual problems associated with stage 3 and 4. Embodiments of the vision therapy system operate in conjunction with traditional procedures in order to address the visual problems as described previously.

Phase I: Enhance the Stability of the Visual Input System

Vision therapy system modules: VME Levels 1-4, OVI Levels 1-4, DOMP Level 1-4, VMI Level 1, 1. Extend range of ocular motility.
2. Develop accurate saccadics with high level motor planning Voluntary saccadic fixation.

Stimulus generated saccadic fixation.

Voluntary and stimulus generated saccadic fixation associated with high-level visual processing tasks such as figure ground, visual closure, spatial computing and balance.

3. Integration of saccadics with balance and visuomotor performance.

4. Integration of saccadics with balance and visuomotor performance adding auditory and visual clues and peripheral distracters.

Phase II: Develop Fusional Sustenance

Standard traditional procedures: VTS3 Computer Orthopter. Vectograms, Brock Strings, loose prisms, stereoscopes etc.

1. Stabilize Binocularity.
2. Develop adequate fusional control: Stereo enhanced and stereo induced.
3. Enhance speed of recovery.
4. Enhance facility of accommodative-convergence.

Phase III: Develop Speed of Visual Information Processing and Stability of Visuomotor Performance Vision therapy system modules: OVI Levels 5 and 6, DOMP Level 5, VMI Levels 3 and 4

1. Develop a stable Vestibular Ocular Reflex (VOR) by integrating sensory stereo fusion and auditory inputs with balance.
2. Enhance visuomotor control associated with changing stimuli in the visual environment.
3. Enhance speed of visual information processing.

Accordingly, an embodiment of the present invention includes a method of using a vision therapy system. The method comprises the steps of enhancing the stability of the visual input system, wherein enhancing the stability of the visual input system comprises performing at least one of a VME module vision therapy, an OVI module vision therapy, a DOMP module vision therapy and a VMI module vision therapy; developing fusional sustenance; and developing speed of visual information processing and stability of visuomotor performance, wherein the developing speed of visual information processing and stability of visuomotor performance comprises performing at least one of an OVI module vision therapy, a DOMP module vision therapy and a VMI module vision therapy.

The use of each module varies with each phase as described in the following.

Visuomotor Enhancer (VME)

This module is the starting point for Phase I of therapy. The clinical goal of Phase I of my therapy sequence is to stabilize the quality of ocular fixation from both a retino-motor basis (input) as well as "top down" frontal-occipital dorsal stream processing (integrative output).

The initial sequence of therapy flows from level 1 (stimulus generated rotation and pursuits) to level 4 (combination of stimulus generated rotations and pursuits and jump saccadic fixation) with the integration of balance into the process.

Each of the 4 levels allows the doctor to load the procedure for increased "brain filtering" and increased integration of multi-sensory processing when appropriate, by adding the Head Sensor, Balance Board, controlling the speed of rotation, type of target and Manual versus Auto changes in rotation. These functions are controlled by adjusting the controls on the Parameters Menu of each level. As the patient progresses, the doctor can apply variable prism monocularly in order to increase the sensory mismatch. Progress eventually to using yoked prism with both eyes open when appropriate.

The vibrating feedback activated by the Head Sensor and the auditory feedback from the Balance Board are the important ingredients for affecting synaptic changes.

Working Distance

The ideal working distance for the VME procedure places the patient 6-10 feet from the projection screen.

VME Level 1 Phase I

VME Level 1 offers two modes: Manual and Auto.

In the Manual Mode, the patient's task is to keep the Hand Shooter Remote's cursor on the assigned target as the rotator wheel revolves. They start by "shooting" the blue target. They will then proceed to "shoot" other targets as the doctor directs them.

In the Auto Mode, the patient's task is to start by "shooting" the blue target and then keep the Hand Shooter Remote's cursor on that target until a different target presents in blue. They will "shoot" the new target and proceed to subsequent targets as presented.

It is recommended to start monocularly with a slow speed of rotation. Stress standing in a balanced position with the feet as wide as the shoulders. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by adjusting speed and use of prism etc. It is important to note that speed is not as important for accuracy. Increase the speed of rotation whenever the patient reaches 95% time on target for two sessions.

The doctor may adjust the Rotational Speed while the procedure is running by pressing the "F2" key on the keyboard. Use the "+" or "−" keys to increase or decrease the rotational speed. Press "F2" again when the adjustment is completed.

A. Instruct the patient to feel their eye/eyes pointing to the target. While they are doing this, they should be aware of their peripheral vision. Work with the patient and encourage them to relax as this will help them to expand their peripheral awareness.

B. When the patient feels that their eye/eyes is/are aimed at the target, they are to shoot it with the Hand Shooter Remote and then follow the rotating target with their eyes. They guide the Hand Shooter Remote and make necessary corrections if the auditory feedback tone sounds alerting them that the remote is off target. They continue until the doctor calls out another target (if in the Manual Mode) or until another blue target appears in the periphery (if the Auto Mode is selected).

It is recommended to start with Manual Mode until the patient attains 95% or greater Time on Target. Then switch to Auto Mode, mixing Random and Sequential options on alternate therapy sessions. The doctor may also change the type of objects to add variety. It is recommended to use Symbols as a higher level of difficulty. For children who don't know the alphabet or aphasic patients who cannot verbalize the alphabet, use the Shapes option. The Revolution checkbox denotes the number of revolutions to be completed before the next target is presented.

On the Parameters Menu, there are three options for direction of rotation: Clockwise, Counterclockwise and Both. Although Clockwise and Counterclockwise direction should be at the same relative level of difficulty for the patient, selecting Both will change the direction randomly and this increases the level of difficulty. It is recommended to use the Both option when the patient achieves 90% accuracy on the assigned task in either the CW or CCW mode.

C. When 80% or greater Time on Target is achieved, add the Head Sensor. Enable the Curser and Rumble boxes for the Head Sensor. This will provide visual cues as well as a vibration of the Hand Shooter Remote when the head is moved rather than the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement.

D. When 95% or greater Time on Target is achieved for each eye, select Binocular from the Parameters Menu and repeat above with both eyes open. Alternate sessions by adding yoked prism to create a visual mismatch when appropriate.

E. Work to develop the patient's ability to be aware of the periphery while attending to the rotating target.

Scoring

Duration: Denotes how long the procedure was actually performed. Targets:
 a. Percentage of Time on Targets equals the percentage of time that the Hand Shooter Remote cursor was on the assigned target.

Head Sensor: Scores the total number of times the patient has moved their head outside of the assigned rings.

Bal. Board: Denotes the percentage of time the patient was off balance and the direction they were off balance.

VME Level 2 with Balance Phase I

VME Level 2 with Balance Phase I combines the therapeutic tasks of VME level 1 with the integration of interactive balance. When VME Level 2 is selected, the Interactive Balance Board will be activated. Repeat the sequence as described in level 1 steps A & B while the patient is on the Balance Board. Enable the Balance Board Cursor and Auditory features which will provide for a visual representation as well as an auditory feedback of their balance.

Instruct the patient to stand on the balance board and have them position themselves according to the instructions in the Balance Board section of the printed Operations Manual.

A. When 80% or greater time on target is achieved, add the Head Sensor. Enable the Curser and Rumble features for the Head Sensor. This will provide a visual cue as well as a vibration of the Hand Shooter Remote when the head is moved instead of the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble features to help them in adjusting and controlling their head movement.

B. When 95% Time on Target or greater is achieved for each eye, select Binocular from the Parameters Menu and repeat above with both eyes open. Add yoked prism on alternate sessions to create a visual mismatch when appropriate.

C. Work to develop the patient's ability to be aware of the periphery while attending to the rotating target.

Scoring

Duration: Denotes how long the procedure was actually performed. Targets:
 a. Percentage of Time on Targets equals the percentage of time that the Hand Shooter Remote cursor was on the assigned target.

Head Sensor: Scores the total number of times the patient has moved their head outside of the assigned rings.

Bal. Board: Denotes the percentage of time the patient was off balance and the direction they were off balance.

VME Level 3 Phase I

VME Level 3 Phase I: Your patient's task is to "shoot" the blue target with the Hand Shooter Remote. After the first target is successfully shot the program will immediately present another target. Your patient should "shoot" the succeeding targets as rapidly and accurately as possible.

VME Level 3 Phase I requires a higher level of "top down processing" than levels 1 and 2. Level 3 adds a random stimulus generated jump saccadic to a smooth ocular rotation. Accurate fixation from one designated target to another requires motor planning (frontal lobe) and dorsal stream processing including spatial relations and visuomotor integration.

A. Have the patient stand in a balanced position with their feet as wide as their shoulders. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by adjusting speed and use of prism etc. Speed is not as important as accuracy. Adjust the speed of rotation according to the patient's progress.

The doctor may adjust the Rotational Speed while the procedure is running by pressing the "F2" key on the keyboard. Use the "+" or "−" keys to increase or decrease the rotational speed. Press "F2" again when the adjustment is completed.

B. Instruct the patient to feel their eye/eyes pointing to the target. While they are doing this they should be aware of their peripheral vision. Work with the patient and encourage them to relax as this will help them to expand their peripheral awareness.

C. Have the patient perform this level with both eyes open. Initially, instruct the patient to feel that their eyes are aimed at the blue target and shoot it with the Hand Shooter Remote. Make the patient aware of the fact that another target in their peripheral field will change to a color immediately after they shoot out the initial target. Their goal is to be aware of where that target is. As quickly and as accurately as possible they should guide the Hand Shooter Remote and shoot that target. They will continue this process for the assigned duration. They will receive audio reinforcement for hit and missed shots. They should visually guide the Hand Shooter Remote to the target until they hear the proper sound. The doctor may change the type of objects to add variety. For children who do not know the alphabet or aphasic patients who cannot verbalize the alphabet use the Shapes option. Do not choose the Red/Blue option as this is assigned for Phase III therapy.

D. It is recommended to initially start by selecting the 4 Objects button. When the patient achieves 85% accuracy or greater of targets successfully shot, increase the level of difficulty by selecting the 8 Object button on the Parameters Menu.

E. When the patient achieves 80% accuracy or greater of targets successfully shot for 2-3 sessions It is recommended to add the Head Sensor. Enable the Curser and Rumble buttons for the Head Sensor. This will provide visual cues as well as a vibration of the remote sensor when the head is moved rather than the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement.

F. Add yoked prism to create a visual mismatch on alternate sessions when appropriate.

G. Work to develop the patient's ability to be aware of the periphery while attending to the rotating target.

Scoring

Duration: Denotes how long the procedure was actually performed.

Targets:
 a. Total Targets equals the number of targets presented.
 b. Percentage of Hits equals targets successfully shot divided by the total shots attempted.
 c. Hits and Misses denotes successful and unsuccessful shots.

Head Sensor: Scores the total number of times the patient has moved their head outside of the assigned rings.

Bal. Board: Denotes the percentage of time the patient was off balance and the direction they were off balance.

VME Level 3 Phase III

In Phase III the option of using Red and Blue targets allows the doctor to monitor if the patient is processing visual information with both eyes simultaneously. More importantly it provides feedback to the patient when they are not processing visual information with both eyes simultaneously. What makes VME unique is this therapeutic feature which enhances and controls the integration of balance, and dynamic eye movement with the processing of sensory visual information with both eyes simultaneously. If one of the visual inputs were inhibited, the patient will not be able to locate the respective target nor be able to successfully shoot the target.

A. Have the patient stand in a balanced position with the feet as wide as their shoulders. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by adjusting speed and use of prism etc. It is important to note that speed is not as important for accuracy. Increase the speed of rotation as appropriate.

The doctor may adjust the Rotational Speed while the procedure is running by pressing the "F2" key on the keyboard. Use the "+" or "−" keys to increase or decrease the rotational speed. Press "F2" again when the adjustment is completed.

B. Your patient will be wearing the provided Red/Blue clip-on classes. Select Red/Blue from the Parameters Menu. Instruct the patient to feel their eyes pointing to the target. While they are doing this they should be aware of their peripheral vision. Work with the patient and encourage them to relax as this will help them to expand their peripheral awareness.

C. Initially, instruct the patient to feel that their eyes are aimed at the target that has a color and to shoot it with the Hand Shooter Remote. Make the patient aware of the fact that another target in their peripheral field will change to a color immediately after they shoot out the initial target and their goal is to be aware of where that target is. As quickly and as accurately as possible they should guide the Hand Shooter Remote and shoot out that target. They will continue this process for the assigned duration. They will receive auditory reinforcement for hit and missed shots. They should visually guide the Hand Shooter Remote to the target until they hear the proper sound. The doctor may change the type of objects to add variety. For children who do not know the alphabet or aphasic patients who cannot verbalize the alphabet use the Shapes option. It is recommended to initially start by selecting the 4 Object button and when the patient achieves 85% accuracy or greater of targets successfully shot, increase the level of difficulty by selecting the 8 Objects button on the Parameters Menu.

D. When the patient achieves 80% accuracy or greater of targets successfully shot for 2-3 sessions It is recommended to add the Head Sensor. Enable the Curser and Rumble buttons for the Head Sensor. This will provide visual cues as well as a vibration of the Hand Shooter Remote sensor when the head is moved rather than the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement Scoring Duration: Denotes how long the procedure was actually performed.

Targets:
 a. Total Targets equals the number of targets presented.
 b. Percentage of Hits equals targets successfully shot divided by the total shots attempted.
 c. Hits and Misses denotes successful and unsuccessful shots.

Head Sensor: Scores the total number of times the patient has moved their head outside of the assigned rings.

Bal. Board: Denotes the percentage of time the patient was off balance and the direction they were off balance.

VME Level 4 with Balance Phase I

VME Level 4 with Balance Phase I combines the therapeutic tasks of VME level 3 with the integration of interactive balance. When VME Level 4 is selected, the Interactive Balance Board will be activated. Repeat the sequence as described in level 3 steps A, B, C, D, E, F, G while the patient is on the Balance Board. Enable the Balance Board Cursor and Auditory features which will provide for a visual representation as well as an auditory feedback of their balance.

Instruct the patient to stand on the Balance Board and have them position themselves according to the instructions in the Balance Board section of the printed Operations Manual.

D. When the patient achieves 80% or greater accuracy of targets successfully shot for 2-3 sessions add the Head Sensor. Enable the Curser and Rumble features for the Head Sensor. This will provide a visual cue as well as a vibration of the Hand Shooter Remote when the head is moved instead of the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble features to help them in adjusting and controlling their head movement.

E. Add yoked prism on alternate sessions to create a visual mismatch when appropriate.

F. Work to develop the patient's ability to be aware of the periphery while attending to the rotating target.

Scoring

Duration: Denotes how long the procedure was actually performed.

Targets:
 a. Total Targets equals the number of targets presented.
 b. Percentage of Hits equals targets successfully shot divided by the total shots attempted.
 c. Hits and Misses denotes successful and unsuccessful shots.

Head Sensor: Scores the total number of times the patient has moved their head outside of the assigned rings.

Bal. Board: Denotes the percentage of time the patient was off balance and the direction they were off balance.

VME Level 4 with Balance: Phase III

A. When the doctor selects VME level 4 with balance the Integrative Balance Board feature will be activated. Instruct the patient to stand on the Balance Board with their shoes off and their feet centered within the marked area of the board. They should adjust their stance, rather than their posture, until the purple cross is centered within the center target. Once the procedure begins, work with the patient to help them be aware of how they feel when they guide the purple cross to the center target and eliminate the auditory tone by adjusting their posture, rather than their stance, on the Balance Board. It is important that the patient use the visual cue to guide them to proprioceptively re-adjust their posture.

Repeat A-D as described in VME Level 3.

Scoring

Duration: Denotes how long the procedure was actually performed.

Targets:
a. Total Targets equals the number of targets presented.
b. Percentage of Hits equals targets successfully shot divided by the total shots attempted.
c. Hits and Misses denotes successful and unsuccessful shots.

Head Sensor: Scores the total number of times the patient has moved their head outside of the assigned rings.

Bal. Board: Denotes the percentage of time the patient was off balance and the direction they were off balance.

Ocular-Vestibular Integration (OVI)

This module is extremely important and effective for enhancing "Top Down" speed of visual processing especially associated with magnocellular and dorsal stream processing. Aspects that are enhanced are: Peripheral awareness, magnocellular "filtering" while performing tasks, visually guided graphomotor movements (dorsal stream VMI), interactive processing of auditory, visual and motor inputs which is important for Vestibular Ocular Reflex (VOR) conditioning/reconditioning.

The initial sequence of therapy flows from level 1 to level 2 which incorporates the Integrative Balance Board. It is recommended that levels 3,4,5,6 not be used until phase III since these levels enhance sensory binocular vision. Each of the levels allows the doctor to load the procedure for increased brain filtering and integration of multi-sensory processing when appropriate by adding the Head Sensor, Integrative Balance Board, amount of Bull's-eyes presented, size of Letter Charts, placement of Bull's-eyes, and the addition of Red/Blue targets and stereopsis. These functions may be adjusted by the controls on the Parameters Menu for each level. As the patient progresses the doctor can change input to create a sensory mismatch by applying variable prism monocularly, lenses, and binocular yoked prism when appropriate. The vibrating feedback of the Hand Shooter Remote and the auditory feedback from the Balance Board are the important ingredients for affecting synaptic changes.

The doctor can select voice instruction by selecting the Voice Assist box on the Parameters Menu. With this box selected, the patient will follow a voice command thereby adding the integration of auditory input to the task. If the doctor unchecks this box, the doctor will be instructing the patient when to make their next ocular fixation, which is a lower level demand.

Working Distance

The ideal working distance for the OVI procedure places the patient 8-10 feet from the projection screen.

OVI Level 1: Phase I

It is recommended to start monocularly, with the patient standing in a balanced position with the feet as wide as the shoulders. Remove the check from the Randomized box so that the targets are presented in a predictable order. Remove the check from the Voice Assist box so that the doctor will be instructing the patient when to initiate their next fixation. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by increasing or decreasing the level of difficulty using any combination of the following:

Add prism monocularly to increase the sensory mismatch.

Change the presentation of the targets to Randomized by checking that box on the Parameters Menu.

Increase the number of Bull's-eyes presented by adjusting the Total Cells slider on the Parameters Menu.

Add peripheral distracters by checking Cell Distraction on the Parameters Menu.

Change the size of the Letter Charts by selecting 3×3 on the Letter Grid box on the Parameters Menu.

Increasing the amount of targets presentation to a specific field vertically and horizontally by adjusting the Horizontal Weight and Vertical Weight sliders on the Parameter Menu. This option is especially useful for patients with visual neglect or visual field loss.

A. Instruct the patient to feel their eye/eyes pointing to the central white dot. While they are doing this they should be aware of their peripheral vision. Work with the patient and encourage them to relax as this will help them to expand their peripheral awareness.

B. When the patient feels that their eye/eyes is/are aimed at the target, instruct the patient to shoot it with the Hand Shooter Remote and then listen for the auditory command instructing them to "Find Target" which is the white Bull's-eye in the periphery. Work with the patient to be aware of where the Bull's-eye is and to guide their Hand Shooter Remote to accurately shoot out the Bull's-eye.

C. As the trial proceeds, the Bull's-eye will be randomly replaced by a Letter Chart. When this occurs instruct the patient to feel their eyes accurately fixating the letters while, keeping them stable and clear, and then guiding the remote to shoot each letter in alphabetical order. A reinforcing auditory tone will occur each time a letter is correctly shot and the letter will then disappear. A different auditory tone will sound when the aim is incorrect and the letter will remain. Encourage the patient to readjust their fixation and guide their Hand Shooter Remote until the proper letter is shot.

When the patient achieves a level of accuracy of 85% on all targets shot for two consecutive sessions, switch to both eyes open. Choose Binocular on the Parameters Menu and add the following options:

Check the Cell Distracter box on the Parameters Menu which will add increasing numbers of pastel colored squares in the periphery as the patient's accuracy of locating Bull's-eyes improves.

Select 3×3 Letter Grids.

Check the Voice Assist box to add voice command.

D. Instruct the patient that when the pastel squares appear in their peripheral vision their goal is to allow their brain to be aware of the squares without being distracted from accurately shooting out Bull's-eye or Letter Targets. Instruct the patient that if their eye/eyes and hand are not in synchronization they will hear an auditory tone which is the alert that they missed the target. They must then readjust their eye/eyes and guide the Hand Shooter Remote back to the target.

E. When 80% or greater accuracy is achieved when shooting the Bull's-eyes, Center and Chart targets, add the Head Sensor. Enable the Curser and Rumble boxes for the Head Sensor. They will provide visual cues as well as a vibration of the Hand Shooter Remote when the head is moved rather than the eyes. Start with the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement.

At any time the doctor can add yoked prisms. Instruct the patient to be aware of their motor adjustment to the sensory miss-match Scoring Duration: Denotes how long the procedure was actually performed.

Bull's-eye: Percentage equals number of Bull's-eyes successfully shot divided by the total shots attempted.

Center: Percentage equals number of successful shots on the Center Bull's-eye divided by the total shots attempted.

Chart: Percentage equals the number of chart targets successfully shot in order divided by the number of charts attempted.

Head Sensor: Scores the total number of times the patient has moved their head outside of the assigned rings.

Bal. Board: Denotes the percentage of time the patient was off balance and the direction they were off balance.

OVI Level 2 with Balance: Phase I

OVI level 2 combines the therapeutic tasks of OVI level 1 with the integration of the Interactive Balance Board. When OVI Level 2 is selected, the Interactive Balance Board will be activated. It is recommended to have the patient perform this level with both eyes open. Instruct them to position themselves on the Balance Board according to the instructions in the Balance Board section of the printed Operations Manual. For this level, enable the Voice Assist box to initiate voice activated commands.

Proceed by following the instructions set described in OVI Level 1: Phase I.

Scoring

Duration: Denotes how long the procedure was actually performed.

Bull's-eye: Percentage equals number of Bull's-eyes successfully shot divided by the total shots attempted.

Center: Percentage equals number of successful shots on the Center Bull's-eye divided by the total shots attempted.

Chart: Percentage equals the number of chart targets successfully shot in order divided by the number of charts attempted.

Head Sensor: Scores the total number of times the patient has moved their head outside of the assigned rings.

Bal. Board: Denotes the percentage of time the patient was off balance and the direction they were off balance.

OVI Level 3 Phase III

A. In Phase III the option of using Red and Blue letters allows the doctor to monitor if the patient is processing visual information with both eyes simultaneously and more importantly provides feedback to the patient when they are not processing visual information with both eyes simultaneously. What makes OVI unique is that the increase in the level of therapeutic control enhances the integration of balance and dynamic eye movement while processing sensory visual information with both eyes simultaneously. If one of the visual inputs were inhibited, the patient will not be able to identify the respective target. And they will not be able to accurately shoot the target.

B. Your patient will be wearing the provided Red/Blue clip-on glasses. Instruct the patient to feel their eyes pointing to the target. While they are doing this they should be aware of their peripheral vision. Work with the patient and encourage them to relax as this will help them to expand their peripheral awareness.

C. For this level enable the Voice Assist box to initiate voice activated commands. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by increasing or decreasing the level of difficulty using any combination of the following:

Change the presentation of the targets to Randomized by checking that box on the Parameters Menu.

Increase the number of Bull's-eyes presented by adjusting the Total Cells slider on the Parameters Menu.

Add peripheral distracters by clicking Cell Distraction on the Parameters Menu.

Change the size of the Letter Charts to Small by selecting Small on the Cell Size option on the Parameters Menu.

Increasing the amount of targets presentation to a specific field vertically and horizontally by adjusting the Horizontal Weight and Vertical Weight sliders on the Parameter Menu. This option is especially useful for patients with visual neglect or visual field loss.

D. Instruct the patient to feel their eye/eyes pointing to the central white dot. While they are doing this they should be aware of their peripheral vision. Work with the patient and encourage them to relax as this will help them to expand their peripheral awareness.

E. When the patient feels that their eyes are aimed at the target, instruct the patient to shoot it with the Hand Remote Sensor and then listen for the auditory command instructing them to "Find Target" which is the white Bull's-eye in the periphery. Work with the patient to help them be aware of where the Bull's-eye is and to guide their Hand Shooter Remote to accurately shoot out the Bull's-eye.

F. As the trial proceeds, the Bull's-eye will be randomly replaced by a Letter Chart. When this occurs instruct the patient to feel their eyes accurately fixating the letters and to be aware of all the letters simultaneously without any of them disappearing. If any letters disappear encourage the patient to blink their eyes and continue this process until all of the letters reappear.

G. Once all the letters are visible and stable, the patient should guide the Hand Shooter Remote to shoot each letter in alphabetical order. A reinforcing auditory tone will occur each time a letter is correctly shot and the letter will then disappear. A different auditory tone will sound when the aim is incorrect and the letter will remain. Encourage the patient to readjust their fixation and guide their Hand Shooter Remote until the proper letter is shot.

H. Instruct the patient that when the pastel squares appear in their peripheral vision their goal is to allow their brain to be aware of the squares without being distracted from accurately shooting out Bull's-eye or Letter Targets. Instruct the patient that if their eye/eyes and hand are not in synchronization they will hear an auditory tone which is the alert that they missed the target and they must then readjust their eye/eyes and guide the Hand Shooter Remote back to the target.

I. When 80% or greater accuracy in shooting all of the targets is achieved, add the Head Sensor. Enable the Curser and Rumble boxes for the Head Sensor. This will provide visual cues as well as a vibration of the Hand Shooter Remote when the head is moved rather than the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement.

Scoring

Duration: Denotes how long the procedure was actually performed.

Bull's-eye: Percentage equals number of Bull's-eyes successfully shot divided by the total shots attempted.

Center: Percentage equals number of successful shots on the Center Bull's-eye divided by the total shots attempted.

Chart: Percentage equals the number of chart targets successfully shot in order divided by the number of charts attempted.

Head Sensor: Scores the total number of times the patient has moved their head outside of the assigned rings.

Bal. Board: Denotes the percentage of time the patient was off balance and the direction they were off balance.

OVI Level 4 with Balance Phase III

OVI level 4 combines the therapeutic tasks of OVI level 3 with the integration of the Interactive Balance Board. Enable the Balance Board Cursor and Auditory features which will provide for a visual representation as well as an auditory feedback of their balance. Instruct the patient to stand on the Balance Board and have them position themselves according to the instructions in the Balance Board section of the printed Operations Manual.

Proceed by following the instructions set described in OVI Level 3: Phase III.

Scoring

Duration: Denotes how long the procedure was actually performed.

Bull's-eye: Percentage equals number of Bull's-eyes successfully shot divided by the total shots attempted.

Center: Percentage equals number of successful shots on the Center Bull's-eye divided by the total shots attempted.

Chart: Percentage equals the number of chart targets successfully shot in order divided by the number of charts attempted.

Head Sensor: Scores the total number of times the patient has moved their head outside of the assigned rings.

Bal. Board: Denotes the percentage of time the patient was off balance and the direction they were off balance.

OVI Level 5 Phase III

Level 5 adds targets options with disparity which results in stereopsis when the level of binocularity is appropriate and stable. The uniqueness of VMI level 5 is that it provides the patient with an interactive experience for stabilizing central fusion by using stereopsis feedback as the patient develops the neurological integration of dynamic ocular motor control, auditory and balance (VOR). Stable binocular fusion is an important input to the Vestibular Ocular Reflex (VOR) which is commonly out of phase in patients with acquired brain injury and other neurological disorders which affect the vestibular processing system.

A. Select the level of disparity by adjusting the Stereo Effect slider bar on the Parameters Menu. It is recommended to place the level at the middle of the slider and increasing the demand as the patient achieves 90% accuracy. A doctor can select Base Out disparity or Base In disparity depending on the diagnosis. When the patient or the doctor selects Base Out disparity one form will appear to be closer than all the rest and the other three will appear to be farther back. The patient is to shoot the form that appears to be closest. With Base In disparity, one form will appear to be further back and the other three will appear to be closer. The patient must shoot the one that appears to be further back. The doctor may also increase or decrease the level of disparity while the procedure is running by pressing the "F2" key on the keyboard. Use the "+" or "−" key to adjust the disparity level. Press "F2" again when the adjustment is completed.

B. Your patient will be wearing the provided Red/Blue clip-on glasses. Instruct the patient to feel their eyes pointing to the target. While they are doing this they should be aware of their peripheral vision. Work with the patient and encourage them to relax as this will help them to expand their peripheral awareness.

C. For this level enable the Voice Assist box to initiate voice activated commands. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by increasing or decreasing the level of difficulty using any combination of the following:

Change the presentation of the targets to Randomized by checking that box on the Parameters Menu.

Increase the number of Bull's-eyes presented by adjusting the Total Cells slider on the Parameters Menu.

Add peripheral distracters by clicking Cell Distraction on the Parameters Menu.

Change the size of the Letter Charts to Small by selecting Small on the Cell Size option on the Parameters Menu.

Increasing the amount of targets presentation to a specific field vertically and horizontally by adjusting the Horizontal Weight and Vertical Weight sliders on the Parameter Menu. This option is especially useful for patients with visual neglect or visual field loss.

D. Instruct the patient to feel their eye/eyes pointing to the central white dot. While they are doing this they should be aware of their peripheral vision. Work with the patient and encourage them to relax as this will help them to expand their peripheral awareness.

E. When the patient feels that their eyes are aimed at the target, instruct the patient to shoot it with the Hand Shooter Remote and then listen for the auditory command instructing them to "Find Target" which is the white Bull's-eye in the periphery. Work with the patient to help them be aware of where the Bull's-eye is and to guide their Hand Shooter Remote to accurately shoot out the Bull's-eye. As the trial proceeds, the Bull's-eye will be randomly replaced by a chart with forms with disparity as described above. When this occurs instruct the patient to feel their eyes accurately fixating the forms and fusing them. They are to shoot out the one that is closest if the Base Out option is selected. They are to shoot the one that appears to be furthest away if the Base In option is selected. If the forms are double, work with the patient to help them fuse using standard therapy techniques for fusion therapy. A reinforcing tone will occur each time a form is correctly shot and the form will then disappear. A different auditory tone will sound when the aim is incorrect and the form will remain. Encourage the patient to readjust their fixation and guide their Hand Shooter Remote until the proper form is shot.

F. Instruct the patient that when the pastel squares appear in their peripheral vision their goal is to allow their brain to be aware of the squares without being distracted from accurately shooting out Bull's-eye or letter targets. Instruct the patient that if their eye/eyes and hand are not in synchronization they will hear an auditory tone which is the alert that they missed the target and they must then readjust their eye/eyes and guide the Hand Shooter Remote back to the target.

G. When 80% or greater accuracy in shooting all of the targets is achieved, add the Head Sensor. Enable the Curser and Rumble boxes for the Head Sensor. This will provide visual cues as well as a vibration of the Hand Shooter Remote when the head is moved rather than the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement.

Scoring

Duration: Denotes how long the procedure was actually performed.

Bull's-eye: Percentage equals number of Bull's-eyes successfully shot divided by the total shots attempted.

Center: Percentage equals number of successful shots on the Center Bull's-eye divided by the total shots attempted.

Chart: Percentage equals the number of chart targets successfully shot in order divided by the number of charts attempted.

Head Sensor: Scores the total number of times the patient has moved their head outside of the assigned rings.

Bal. Board: Denotes the percentage of time the patient was off balance and the direction they were off balance.

OVI Level 6 with Balance Phase III

OVI level 6 combines the therapeutic tasks of OVI level 5 with the integration of the Interactive Balance Board. Enable the Balance Board Cursor and Auditory features which will provide for a visual representation as well as an auditory feedback of their balance. Instruct the patient to stand on the Balance Board and have them position themselves according to the instructions in the Balance Board section of the printed Operations Manual.

Proceed by following the instructions set described in OVI Level 5: Phase III.

Scoring

Duration: Denotes how long the procedure was actually performed.

Bull's-eye: Percentage equals number of Bull's-eyes successfully shot divided by the total shots attempted.

Center: Percentage equals number of successful shots on the Center Bull's-eye divided by the total shots attempted.

Chart: Percentage equals the number of chart targets successfully shot in order divided by the number of charts attempted.

Head Sensor: Scores the total number of times the patient has moved their head outside of the assigned rings.

Bal. Board: Denotes the percentage of time the patient was off balance and the direction they were off balance.

Dynamic Ocular Motor Processing (DOMP)

Overview

As with the OVI module, this module is extremely important and effective for enhancing "Top Down" speed of visual processing especially associated with magnocellular and dorsal stream processing. Aspects that are enhanced are: Peripheral awareness, magnocellular "filtering" while performing parvocellular tasks, visually guided graphomotor movements (dorsal stream VMI), interactive processing of auditory, visual and motor inputs, important for Vestibular Ocular Reflex (VOR) conditioning/reconditioning. This module presents procedures which require a higher level of visual processing than OVI because of the addition of contour interaction (magnocellular) and associated random cues for ocular fixation (parvocellular), spatial relations, visual sequencing and visual organization.

The initial sequence of therapy flows from Level I, which is a combination of voluntary initiated saccadics and visually guided graphomotor performance (visual motor integration), to Levels 2 and 3 which add increasingly random visual cues to initiate stimulus generated saccadics. Level 4 increases the level of processing tasks using spatial relations and adds auditory and visual motor matching.

Although the modules can be used in any sequence, It is recommended to start with level 1 and increasing the demand by changing the stimulus to symbols as soon as possible. Level 2 should progress from minimum stimuli to full grid then progressing to level 3. Levels 4 and 5 should follow when the patient is achieving 98% or greater on levels 2 and 3. Level 4 and 5 are excellent for developing dynamic visually guided graphomotor control and it is recommended to use these modules early in therapy as the patient approaches 75% accuracy on levels 1-3. For level 4 and 5 it is not recommended to use the binocular and stereopsis options until phase III.

Each of the levels allow the therapist to load the procedure for increased brain filtering and integration of multi-sensory processing when appropriate, by adding the Head Sensor, Interactive Balance Board, type of Targets, number of Stimuli, and the addition of Red/Blue Targets and stereopsis. These functions may be adjusted using the controls located on the Parameters Menu for each level. As the patient progresses the doctor may change input to create a sensory mismatch by applying variable prism monocularly, lenses, and binocular yoked prism when appropriate. The vibrating feedback of the Hand Shooter Remote and the auditory feedback from the balance board are the important ingredients for affecting synaptic changes.

Working Distance

The ideal working distance for the DOMP procedure places the patient 8-10 feet from the projection screen.

DOMP Level I Phase I:

It is recommended to start monocularly, with the patient standing in a balanced position with their legs as wide as the shoulders. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by increasing or decreasing the level of difficulty using any combination of the following:

Add prism monocularly to increase the sensory mismatch.

Increase the number of targets presented by selecting Full Grid on the Parameters Menu.

Change targets to Symbols in the Target box on the Parameters Menu.

A. Work with the patient and encourage them to relax as this will help them to expand their peripheral awareness of the entire chart.

B. When the patient feels that they are aware of the entire chart, instruct them to then jump their eye/eyes to the appropriate target that the doctor selected on the Parameters Menu. For example, if the doctor select First and Last on the Cell Order option, then the patient must move their eye/eyes and find the first target of each line then guide the Hand Shooter Remote and shoot it. Then move their eye/eyes to the last target on the line and then guide the Hand Shooter Remote and shoot that target as well. If they accurately shoot the target they will hear a reinforcing auditory tone. If they are not accurate or if they lose their place and shoot the wrong target an auditory tone will sound. Only when the patient feels that they are looking straight on the target should they visually guide the Hand Shooter Remote to shoot the target. Note, if the patient's shot misses the target they should not attempt to re-shoot it, they should simply shoot the next assigned target. Instruct the patient to be aware of the entire grid while aiming their eye/eyes to the next selected target and then guide the Hand Shooter Remote and shoot it. Stress the importance of accurate left to right sequencing.

C. When the patient achieves a level of accuracy of 85% on all targets shot for two consecutive sessions, have them perform the procedure with both eyes open. Choose Binocular on the Parameters Menu and add the following options:

Check Full Grid on the Parameters Menu which will add more targets.

Select Symbols for type of target.

D. When 80% or greater accuracy is achieved for all targets shot, add the Head Sensor. Enable the Curser and Rumble buttons for the Head Sensor. This will provide visual cues as well as a vibration of the Hand Shooter Remote when the head is moved rather than the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement.

E. At any time the doctor can add yoked prisms. Instruct the patient to be aware of their motor adjustment to the sensory mismatch.

Scoring

Duration: Denotes how long the procedure was actually performed.

Targets: Percent equals the number of successful shots divided by the total shots attempted.

Head Sensor: Scores the total number of times the patient has moved their head outside of the assigned rings.

Bal. Board: Denotes the percentage of time the patient was off balance and the direction they were off balance.

DOMP Level 2 Phase I

Level 2 increases the demand for brain filtering and accuracy of ocular motor performance by adding cues which require accurate stimulus generated saccadic fixations (parvocellular) while simultaneously processing magnocellular processing to guide the eyes and the Hand Shooter Remote in a left to right sequence. It is recommended to start monocularly, with the patient standing in a balanced position with the legs as wide as their shoulders. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by increasing or decreasing the level of difficulty using any combination of the following:

Add prism monocularly to increase the sensory mismatch.

Increase the number of targets presented by selecting Full Grid on the Parameters Menu.

Increase the number of Cells underscored per line in the Differences per Row box on the Parameters Menu.

Change targets to Symbols in the target box on the Parameters Menu.

Proceed by following the instructions set described in A-E in DOMP Level 1 Phase I.

Scoring

Duration: Denotes how long the procedure was actually performed.

Targets: Percent equals the number of successful shots divided by the total shots attempted.

Head Sensor: Scores the total number of times the patient has moved their head outside of the assigned rings.

Bal. Board: Denotes the percentage of time the patient was off balance and the direction they were off balance.

DOMP Level 3 Phase I

Level 3 increases the demand for brain filtering and accuracy of ocular motor performance by adding cues which require accurate stimulus generated saccadic fixations (parvocellular) while simultaneously processing magnocellur processing to guide the eyes and the Hand Shooter Remote in a left to right sequence. In this level the underscored Cells will be random and without a fixed amount per line. It is recommended to start monocularly, with the patient standing in a balanced position with the legs as wide as their shoulders. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by increasing or decreasing the level of difficulty using any combination of the following:

Add prism monocularly to increase the sensory mismatch.

Increase the number of Cells presented by selecting Full Grid on the Parameters Menu.

Increase the number of random Cells underscored by adjusting the Stimuli Number slider on the Parameters Menu.

Change targets to Symbols in the target box on Parameters Menu.

Proceed by following the instructions set described in A-E in DOMP Level 1 Phase I.

Scoring

Duration: Denotes how long the procedure was actually performed.

Targets: Percent equals the number of successful shots divided by the total shots attempted.

Head Sensor: Scores the total number of times the patient has moved their head outside of the assigned rings.

Bal. Board: Denotes the percentage of time the patient was off balance and the direction they were off balance.

DOMP Level 4 Phase I

Level 4 increases the demand for brain filtering and accuracy of ocular motor performance by adding cues which require the processing of visual spatial coordinates (spatial relations) matched to an auditory command. It is recommended to perform this procedure with both eyes open and selecting Binocular on the Parameters Menu, with the patient standing in a balanced position with the legs as wide as their shoulders. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by increasing or decreasing the level of difficulty using any combination of the following:

Increase the number of Cells by selecting Full Grid on the Parameters Menu.

Change targets to Symbols in the Target box on the Parameters Menu.

A. Work with the patient and encourage them to relax as this will help them to expand their peripheral awareness of the entire chart.

B. When the patient feels that they are aware of the entire chart instruct the patient to listen to the auditory command and then visualize where the intersection of the two coordinates meet and to shoot the target that is in that Cell. If they accurately shoot the targets they will hear a reinforcing auditory tone. If they locate and shoot the incorrect target they will hear a different auditory tone. To add a visual-auditory-match, instruct the patient to call out the target in that Cell and then shoot it.

This is an excellent visualization skill for patients with aphasia. When the patient achieves a level of accuracy of 85% on all targets shot for two consecutive sessions, have them perform the procedure with both eyes open. Choose Binocular on the Parameters Menu and add the following options:

C. Check Full grid on the Parameters Menu which will add more targets.

D. Select Symbols for type of target.

E. When 80% or greater accuracy is achieved add the Head Sensor. Enable the Curser and Rumble buttons for the Head Sensor. This will provide visual cues as well as a vibration of the Hand Remote Shooter when the head is moved rather than the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement.

F. At any time the doctor can add yoked prisms. Instruct the patient to be aware of their motor adjustment to the sensory mismatch.

Scoring

Duration: Denotes how long the procedure was actually performed.

Targets: Percent equals the number of successful shots divided by the total shots attempted.

Head Sensor: Scores the total number of times the patient has moved their head outside of the assigned rings.

Bal. Board: Denotes the percentage of time the patient was off balance and the direction they were off balance.

DOMP Level 5 Phase I

The therapeutic goal of this level is to enhance visually guided, graphomotor performance, modulated through the process of motor planning. This level can be initiated at any phase of the therapy however it is recommended to use the following guidelines:

1. Initially prescribe this level monocularly, in Phase I, as the patient works with VME level 3 and 4 in conjunction with DOMP Level 5. Do not use the red/blue option or the stereo option in the Target box at this level.

2. Work this level with both eyes open when the patient is working in conjunction with VME level 3 and 4 with both eyes open.

A. Begin with the patient standing in a balanced position with the legs as wide as their shoulders. Instruct the patient to be aware of the proprioceptive feel of their eyes moving and assign a scale so that the patient can rate their level of feedback. For example (1-5), 1 represents no feeling and 5 represents pain. It is recommended to keep the level around 3.5 by increasing or decreasing the level of difficulty using any combination of the following:

Add prism monocularly to increase the sensory mismatch.

Make the Chart smaller by selecting Cell Size Small on the Parameters Menu.

B. Work with the patient and encourage them to relax as this will help them to expand their peripheral awareness of the entire chart.

C. When the patient feels that they are aware of the entire screen of charts, instruct the patient to locate chart number one and then to aim their eye/eyes and guide the Hand Shooter Remote. When they feel that the chart is clear they are to shoot out the chart number 1. If they shoot accurately, they will hear a reinforcing auditory tone. If they are inaccurate or select the wrong chart in sequential order they will hear a different auditory tone. Instruct the patient to continue this process until they shoot out all charts in numerical order. As they shoot out the charts, they will be replaced with letters. Your patient is to aim their eye/eyes and when they see the letters are clear and stable they are to carefully aim the Hand Shooter Remote and shoot out the letters in alphabetical order. If they are accurate they will hear a reinforcing auditory tone. If they are inaccurate or do not select and shoot the letters in alphabetical order they will hear a different auditory tone.

D. When the patient achieves a level of accuracy of 85% on all targets shot for two consecutive sessions, have them perform the procedure with both eyes open. Choose Binocular on the Parameters Menu and add the following options:

E. Make the size of the Chart smaller by selecting Small on the Cell Size option. Add more letters to shoot out by increasing the number of Cells in the Number of Targets box.

F. When 80% or greater accuracy is achieved add the Head Sensor. Enable the Curser and Rumble buttons for the Head Sensor. This will provide visual cues as well as a vibration of the Hand Shooter Remote when the head is moved rather than the eyes. Start the Head Sensor sensitivity level at 5 rings and use the feedback to help the patient monitor and control their head movement. Work towards a goal of increasing the sensitivity to 2 rings. Instruct the patient to use the green cursor and the Rumble feature to help them in adjusting and controlling their head movement.

G. At any time the doctor can add yoked prisms. Instruct the patient to be aware of their motor adjustment to the sensory mismatch Scoring Duration: Denotes how long the procedure was actually performed.

Targets: Percent equals the number of successful shots on the target box divided by the total shots attempted.

Chart: Percent equals the number of chart targets successfully shot in order divided by the total charts attempted.

Head Sensor: Scores the total number of times the patient has moved their head outside of the assigned rings.

Bal. Board: Denotes the percentage of time the patient was off balance and the direction they were off balance.

DOMP Level 5 Phase III

DOMP Level 5 provides the option of using Red and Blue targets and allows the doctor to monitor if the patient is processing visual information with both eyes simultaneously and more importantly provides feedback to the patient when they are not processing visual information with both eyes simultaneously.

What makes this therapeutic feature unique is that it enhances and controls the integration of balance, and dynamic eye movement with the processing of sensory visual information with both eyes simultaneously. If one of the visual inputs is inhibited, the patient will not be able to locate the respective target and they will not be able to successfully shoot out the target. Your patient will be wearing the provided Red/Blue clip-on glasses. Select Red/Blue from the target box option on the Parameters Menu. Instruct the patient to feel their eyes pointing to the target. While they are doing this they should be aware of their peripheral vision. Work with the patient and encourage them to relax as this will help them to expand their peripheral awareness.

A. Repeat DOMP Level 5 Phase I steps B-G.

B. When the patient achieves an accuracy of 85% add stereopsis as described in the next paragraph.

DMP level 5 also provides for targets options with disparity which results in stereopsis when the level of binocularity is appropriate and stable. The uniqueness of this feature is that it provides the patient with an interactive experience for stabilizing central fusion by using stereopsis feedback, as the patient develops the neurological integration of dynamic ocular motor control, auditory and balance (VOR). Stable binocular fusion is an important input to the Vestibular Ocular Reflex (VOR) which is commonly out of phase in patients with acquired brain injury and other neurological disorders which affect the vestibular processing system.

Select Stereo from the Target Option box on the Parameters Menu. Select the level of disparity by adjusting the Stereo Effect slider bar on the Parameters Menu. It is recommended to place the level at the middle of the slider and increasing the demand as the patient achieves 90% accuracy. The doctor may also increase or decrease the level of disparity while the procedure is running by pressing the "F2" key on the keyboard. Use the "+" or "−" key to adjust the disparity level. Press "F2" again when the adjustment is completed. The doctor can select Convergence disparity or Divergence disparity depending on the diagnosis. When the doctor selects Convergence disparity one form will appear to be closer than all the rest and the others three will appear to be farther back. The patient is to shoot out the form that appears to be closest. With Divergence stereopsis, one form will appear to be further back and the other three will appear to be closer. The patient must shoot out the one that appears to be further back. Your patient will be wearing the provided Red/Blue clip-on glasses. Instruct the patient to feel their eyes pointing to the target. While they are doing this they should be aware of their peripheral vision. Work with the patient and encourage them to relax as this will help them to expand their peripheral awareness.

Repeat DOMP Level 5 Phase I steps B-G.

Scoring

Duration: Denotes how long the procedure was actually performed.

Targets: Percent equals the number of successful shots on the target box divided by the total shots attempted.

Chart: Percent equals the number of chart targets successfully shot in order divided by the total charts attempted.

Head Sensor: Scores the total number of times the patient has moved their head outside of the assigned rings.

Bal. Board: Denotes the percentage of time the patient was off balance and the direction they were off balance.

Visuomotor Integration (VMI)

The procedures in this module are designed to enhance fixation and stimulus generated ocular pursuits associated with visually guided graphomotor performance.

VMI Level 1 is an excellent procedure for enhancing graded visuomotor control. The level of difficulty flows from using a computer generated visual line to guide the patient, progressing to a level which requires the patient to visualize the direction (no line) and guide the Hand Shooter Remote's cursor to the target.

In VMI Level 2, the patient visually "pushes" a golf cart by aiming the Hand Shooter Remote's cursor on the golf cart and visually directing it to the target flag. The doctor may vary the level of difficulty for the visually guided movements control by establishing a sequence for the patient to guide the golf cart around obstacles found on the golf course.

VMI Level 3 increases the level of demand by randomly changing the speed of the stimulus (golf cart) while the patient is instructed to match the movement by visually tracking the golf cart while using the Hand Shooter Remote to keep the cursor on target. This procedure develops accurate visually guided eye movements associated with spatial relations, motor planning and graded visuomotor integration.

It is recommended to use VMI Levels 1-3 early in Phase 1, after the patient progresses through OME. The importance of the VMI procedures is to stabilize fixation and develop visually guided pursuits as a foundation for higher level dynamic saccadic performance in addition to well controlled binocular vision. The VMI procedures should be performed monocularly until 80% accuracy time on target is achieved.

VMI Level 4 adds a higher level of Top Down processing associated with visuomotor integration skills. It is recommended to use this procedure in Phase III once stable fusion control is demonstrated. For this procedure, a stimuli (code) associated with a letter or number is presented for a predetermined time at the top of the screen and then the stimuli disappears. Your patient is instructed to memorize the stimuli and then visually guide the Hand Shooter Remote's cursor through obstacles to a grid of stimuli at the bottom of the screen. They then shoot the correct stimuli.

Each of the VMI Levels allow the doctor to load the procedure for increased brain filtering and integration of multisensory processing when appropriate, by adding the Head Sensor, and/or Interactive Balance Board. These functions may be adjusted using the controls located on the Parameters Menu for each level. As the patient progresses, the doctor may change input to create a sensory mismatch by applying binocular yoked prism when appropriate. The vibration feedback of the Hand Shooter Remote plus the auditory feedback from the Balance Board are important ingredients for affecting synaptic changes.

Working Distance

The ideal working distance for the VMI procedure places the patient 8-10 feet from the projection screen.

Instruct the patient to be aware of the proprioceptive feel of their eyes moving and assign a scale so that they can rate the level of feedback. For example (1-5), 1 represents no feeling and 5 represents pain. It is recommended to keep the level around 3.5 by adjusting speed and use of prism.

When appropriate repeat above with both eyes open adding yoked prism lenses.

When using VMI Level 2, work with the patient and help them to expand their peripheral awareness in order to avoid the obstacles along the golf course.

When using VMI Level 2 the doctor may increase the demand by assigning sequences for the patient to move the golf cart around obstacles as they guide the golf cart to the flag.

Add the balance board as soon as possible

VMI Level 1 Phase I

Instruct the patient to aim their eye/eyes at the presented letter and shoot it with the Hand Shooter Remote. A line will appear connecting the letter to a number. The goal is for the patient to place the Hand Shooter Remote's cursor on the line and trace this line to the corresponding number. Encourage the patient to feel their eyes following the line. Instruct them to allow their eyes to guide their hand movements while keeping the remote's cursor on the line, until reaching the number at the end of the line and then accurately shoot the number.

If the patient loses fixation, an auditory tone sounds as an alert that the eye/eyes and hand are not in synchronization. The auditory tone alert provides VMI feedback to the patient indicating that they have lost fixation and they should then re-adjust their fixation and keep the remote's cursor on the line.

Scoring

Duration: Denotes how long the procedure was actually performed.

Targets: Percentage On Target Time equals the percent of time that the Hand

Shooter Remote's cursor was "on the line".

Accuracy: Percentage equals the number of stimuli successfully shot divided by the total shots attempted.

Head Sensor: Scores the total number of times the patient has moved their head outside of the assigned rings.

Bal. Board: Denotes the percentage of time the patient was off balance and the direction they were off balance.

VMI Level 2 Phase I

Instruct the patient to feel their eye/eyes fixating on the golf cart while being aware of the entire golf course. Your patient is to then guide the Hand Shooter Remote's cursor and shoot the golf cart to activate it. An auditory tone will sound when the golf cart has been activated. The goal is for the patient to visually "push" the golf cart with the Hand Shooter Remote to the flags in sequential order, without hitting the obstacles on the course.

When the golf cart reaches the first flag, they will hear the sound of the ball dropping in the cup. The background scene will move so that the next flag is visible. They must then move the Hand Shooter Remote's cursor back to the golf cart and shoot it to begin the sequence again. An auditory alert tone will sound if the golf cart collides with an obstacle.

Scoring

Duration: Denotes how long the procedure was actually performed.

Accuracy: Percentage equals the number of flags collected divided by the number of collisions.

Head Sensor: Scores the total number of times the patient has moved their head outside of the assigned rings.

Bal. Board: Denotes the percentage of time the patient was off balance and the direction they were off balance.

VMI Level 3 Phase I

Instruct the patient to feel their eye/eyes fixating the golf cart while being aware of the entire golf course. Your patient is to then guide the Hand Shooter Remote's cursor and shoot the golf cart. An auditory tone will sound and the golf cart will begin to move. The goal is for the patient to maintain ocular fixation on the golf cart while guiding the Hand Shooter Remote's cursor to remain on the golf cart as it moves around the course to the appropriate flags. The uniqueness of this level is that the speed of the golf cart randomly changes. The Parameters Menu allows the doctor to set a minimum and maximum speed range that the gold cart travels between. This develops a higher level of visuomotor control. An auditory alert tone will sound if the Hand Shooter Remote's cursor is not on target.

Scoring

Duration: Denotes how long the procedure was actually performed.

Targets: Percentage On Target Time equals the percent of time that the Hand Shooter Remote's cursor was "on the golf cart".

Head Sensor: Scores the total number of times the patient has moved their head outside of the assigned rings.

Bal. Board: Denotes the percentage of time the patient was off balance and the direction they were off balance.

VMI Level 4 Phase I

Once the VMI Level 4 procedure has been launched the patient will be presented with a screen displaying a central maze. A Bull's-eye target will be displayed at the top of the screen and two rows of stimuli will be displayed at the bottom of the screen. The top row of stimuli represents the Key and the bottom row represents the Code. The Parameters Menu allows the doctor to select either Numbers, Letters, or Symbols for the Key and Code stimulus. For this illustration we will assign Numbers to the Key stimulus and Letters to the Code stimulus.

To begin this procedure, instruct the patient to aim their eye/eyes and Hand Shooter Remote to shoot the Bull's-eye at the top of the screen. Immediately, the Bulls-eye will be replaced by one of the Key Numbers.

Instruct the patient to visualize the Number and then to move their eye/eyes to the bottom of the screen and visualize the Code Letter that is directly below that Number. After a predetermined time, which the doctor may set from the Parameters Menu, the Number at the top of the screen will be replaced by the row of Code Letters from the bottom of the screen. Instruct the patient to continue to visualize the association of the Key Number and the Code Letter.

Next, instruct the patient to aim their eye/eyes at the Letter at the top of the screen that was associated with the Key Number at the bottom of the screen and shoot it with the Hand Shooter Remote. Your patient's goal is to guide this Letter with the Hand Shooter Remote slowly through the openings in the maze and to deliver the Letter to the associated Number on the bottom of the screen without touching any of the maze lines. Encourage the patient to feel their eyes guiding the Letter and to continue to visualize the Letter and its associated Number.

Accuracy of visuomotor integration as well as the ability to hold a visualized pattern is the goal of this procedure. As the patient guides the Letter through the openings of the maze, if their visuomotor control is not accurate and they touch any of the maze lines, they will hear an auditory alert tone. When this occurs the patient should readjust the Letter and continue to visually guide it through the maze openings.

VMI Level 4 Phase 3

Phase III therapy incorporates two option modes which are specific for Phase 3 therapy:

Option one, Monocular Fixation in a Binocular Field.

Option two, Red/Blue targets for developing binocular stability.

If the doctor chooses the Monocular Fixation in a Binocular Field option the program presents the targets in blue and uses a filtering red eye patch over the non-amblyopic eye. This allows the doctor to monitor if the patient is processing visual information with both eyes simultaneously and more importantly, provides feedback to the patient when they are not processing visual information with both eyes simultaneously. If one of the visual inputs were inhibited, the patient will not be able to identify the respective target. They will not be able to accurately identify the maze lines and they will not be able to match the number with its associated letter. This option provides a powerful tool for treating cortical inhibition of vision associated with amblyopia, visual neglect and other cortical insults associated with reduced vision.

If the doctor chooses the binocular option, the patient will use the Red/Blue clip-on glasses. Binocular posture and stability is enhanced since the Letter and Maze opening will be Red and Blue respectively. This requires dynamic control of binocularity integrating balance and dynamic eye movement while processing sensory visual information with both eyes simultaneously. This is a unique feature of embodiments of the vision therapy system.

Scoring

Key Percentage: Denotes the percentage of accuracy shooting the Key stimuli.

Code Percentage: Denotes the percentage of accuracy shooting the Code stimuli.

Collisions: Denotes the number of times that the stimulus touches a maze line.

Average Completion: Denotes the average time necessary to move the stimulus from the top of the maze to the bottom of the maze.

Head Sensor: Scores the total number of times the patient has moved their head outside of the assigned rings.

Bal. Board: Denotes the percentage of time the patient was off balance and the direction they were off balance.

Fixation Anomalies (FA)

The Fixation Anomalies module contains three interactive therapy procedures designed to enhance fixation anomalies associated with intrusion fixation, nystagmoid fixation, eccentric fixation and associated crowding phenomenon.

The three procedure progressively increase the demand for neural re-calibration of retino-motor and retino-spatial processing. The Fixation Anomalies module adds the therapeutic power of the auditory alert tones provided by the Hand Shooter Remote, Head Sensor and the Interactive Balance Board to enhance the effects of biofeedback through top down processing. It is recommended that all three procedures are incorporated in Phase I of the treatment program.

The doctor may add Red and Blue targets to FA Level 2 and FA Level 3. With FA Level 2, in conjunction with the use of the red blue goggles, binocular processing at a sensory level is controlled and reinforced. With FA Level 3, the serpentine line is white while the letters and cross hatched lines are red and blue, thus providing a fusion control as the patient directs ocular motor and fixation control. If fusion breaks down, the white line will split into a red and blue line alerting the patient to re-calibrate fusion.

For FA Levels 2 and 3, the width of the space between the hatch lines can be increased or decreased while the procedure is running by using the +/− keys on the keyboard.

Working Distance

The ideal working distance for the FA procedure places the patient 6-8 feet from the projection screen.

FA Level 1 Phase 1

This is a powerful therapeutic procedure designed to stabilize the steadiness of fixation which helps to enhance the quality of the visual input. Although this procedure is appropriate for all patients with unsteady fixation, it is extremely valuable when treating patients who have intrusion fixation syndrome, nystagmus, eccentric fixation (amblyopia), and other retino-motor deficits.

The procedure capitalizes on the concept of biofeedback, bringing it to a higher level of neural learning by using the auditory alert tones of the Hand Shooter Remote and the vibration feedback associated with the Head Sensor.

Your patient is presented with projected cells, each one containing a pattern of dots. Randomly throughout this projection some cells will have an underscored line. The goal is to have the patient move their eye slowly from left to right until they reach a cell with an underscore line. At that point, the patient should adjust their eye alignment so that they see the dots as clear as possible and as stable as possible.

Once the patient senses that they are aiming their eye accurately, they are to direct the Hand Shooter Remote and place the remote's cursor on the first dot in the cell. Once they feel that they are accurately aligned, they are too slowly squeeze the trigger on the Hand Shooter Remote and shoot the dot. They are instructed to immediately control fixation and keep the remote's cursor on the dot. The goal is to keep the cursor steady on the dot for the period of time which is set from the Parameter Option menu. Each time that fixation is lost and the Hand Shooter Remote's cursor comes off of the dot, an auditory tone will sound which is an alert for the patient to re-calibrate their fixation and fixate back on target.

Once they can sustain fixation for the programmed time they move to the next dot in the cell. Although they will only earn a point if they can stay on target for the programmed time, the repeated re-calibration of fixation in response to the auditory alert tone is the important ingredient in stabilizing fixation. Your patient continues the procedure until all underscored cells are completed. Note that this procedure is performed monocularly.

As the patient improves add the head sensor and then finally the integrated balance board Scoring:
Accuracy:
Dots Successfully Maintained
Dots Unsuccessfully Maintained
Percent Successfully Maintained Head Sensor: Scores the total number of times the patient has moved their head outside of the assigned rings.

Bal. Board: Denotes the percentage of time the patient was off balance and the direction they were off balance.

FA Level 2 Phase I

Your patient begins by shooting the Central Bull's Eye. Instruct the patient to relax and to feel their eyes fixating the left dot of the first line in the first line group on the left. When they see/feel that the dot is steady and clear, they are to aim and place the Hand Shooter Remote's cursor on the dot, and then squeeze the trigger of the Hand Shooter Remote and shoot the dot. A correct response is reinforced by an auditory tone and an incorrect response is reinforced by a different auditory tone. Once they successfully shoot the dot they are too slowly trace the line with the Hand Shooter Remote's cursor until they reach the bottom dot. They shoot that dot and continue to the next line or group. Once the patient has shot the last dot, they will shoot the number displayed on the bottom of the screen that corresponds to the number of hatch lines they have shot.

The most important therapeutic outcome is that the patient can sustain fixation and an accurate visuomotor act as they trace the line. The power of this program is the auditory cue provided to the patient whenever they go off of the line and the neural recalibration in response to this cue as the patient re-fixates and traces accurately. Therefore it is important that the doctor stress to the patient that they must perform this task slowly and deliberately.

As the patient progresses the doctor can adjust the separation of the lines moving them closer to each other thus making the task more difficult by using the +/− keys on the keyboard.

FA Level 2 Phase III

This procedure is designed for enhancing dynamic binocular stability and ocular motor control. The goal is to generalize the static fusional skills developed in Phase II of fusion therapy using the more static procedures such as vectograms, VTS etc. to a more dynamic process. Choose Red/Blue from the Parameter Menu and have the patient perform the above sequence of therapy again. Since the doctor has stabilized fixation and visuomotor control in Phase I of the therapy program, the neural recalibration response to the auditory alert cues enhances the stability of the binocular system at a sensory motor level Scoring:
Accuracy: Percentage of Time On Target
Line Count: Percentage Of Correct Responses
Head Sensor: Scores the total number of times the patient has moved their head outside of the assigned rings.
Bal. Board: Denotes the percentage of time the patient was off balance and the direction they were off balance.

FA Level 3 Phase I

Instruct the patient to relax and to feel their eyes looking at the letter "A" at the top edge of the serpentine line and shoot it. Once they successfully shoot the letter, they are too slowly trace the line with the Hand Shooter Remote's cursor until they reach the crossed hatched lines. When they reach the lines, they are to shoot the dot on the left side and then trace the line with the Hand Shooter Remote until they reach the dot on the right. They must shoot that dot and then continue to the next line or group. Once the patient has shot the last dot they will follow the serpentine line to the letter "B" and shoot it. They then will shoot the number displayed on the bottom of the screen that corresponds to the number of hatch lines they have shot.

Note: It is helpful to tell the patient to visualize the serpentine line as a road that they are riding upon. They always shoot they first dot on the left as in encounter the groups of hatch lines.

The most important therapeutic outcome is that the patient can sustain fixation and sustain an accurate visuomotor act as they trace the serpentine line and then the cross hatched lines. The power of this program is the auditory cue provided to the patient whenever they go off of the line and the neural recalibration in response to this cue as the patient re-fixates and traces again. Therefore it is important that the doctor stress to the patient that they must perform this task slowly and deliberately.

As the patient progresses the doctor can adjust the separation of the lines moving them closer to each other thus making the task more difficult by using the +/− keys on the keyboard.

FA Level 3 Phase III

This procedure is designed for enhancing dynamic binocular stability and ocular motor control. The goal is to generalize the static fusional skills developed in Phase II of fusion therapy using the more static procedures such as vectograms, VTS etc. to a more dynamic process. Choose Red/Blue from the Parameter Menu and have the patient perform the above sequence of therapy again. Since the doctor has stabilized fixation and visuomotor control in Phase I of the therapy program, the neural recalibration response to the alert cues enhances the stability of the binocular system at a sensory motor level. The goal is to trace the serpentine line with the Hand Shooter Remote as in Phase I. However the use of the red blue colors and goggles make this an excellent procedure for developing binocular stability associated with higher level visual processing. The goal is to keep the serpentine line fused while tracing as described in Phase I.

Scoring:
Accuracy:
Percentage Of Time on Serpentine Line
Percentage Of Time on Hatched Lines
Head Sensor: Scores the total number of times the patient has moved their head outside of the assigned rings.
Bal. Board: Denotes the percentage of time the patient was off balance and the direction they were off balance.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A method of using a vision therapy system having a computer operating the system, a projector projecting visual graphics, a display for displaying the projection, and input devices for providing interaction by the user with the system, the method comprising:
   initiating first phase of a vision therapy of enhancing the stability of the visual input system, wherein enhancing the stability of the visual input system comprises performing at least one of a first phase VME module vision therapy, a first phase OVI module vision therapy, a first phase DOMP module vision therapy and a first phase VMI module vision therapy;
   initiating second phase of the vision therapy of developing fusional sustenance; and
   initiating third phase of the vision therapy of developing speed of visual information processing and stability of visuomotor performance, wherein the developing speed of visual information processing and stability of visuomotor performance comprises performing at least one of a third phase VME module vision therapy, a third phase OVI module vision therapy, a third phase DOMP module vision therapy and a third phase VMI module vision therapy.

2. The method of claim 1, wherein performing one of the first or third phase VME module vision therapy comprises providing a target on a display in response to running of a software product; rotating the target at a particular speed; locating a hand controlled remote indicator on the target on the display; shooting the target in response to depression of a trigger of a hand controlled remote; and providing feedback as to whether head and/or body motion is detected from a head sensor and/or balance board respectively.

3. The method of claim 2, wherein the first phase VME module vision therapy includes four levels and the third phase VME module vision therapy includes two levels.

4. The method of claim 1, wherein performing one of the first or third phase OVI module vision therapy comprises providing a target on a display in response to running of a software product; locating the target in a peripheral view of a user defined by the user directing the user's eyes straight at the display; directing a user to locate the target with his eyes; locating a hand controlled remote indicator on the target on the display; shooting the target in response to depression of a trigger of a hand controlled remote; and sounding an auditory alert that the target has been shot.

5. The method of claim 4, further comprising providing feedback as to whether head and/or body motion is detected from a head sensor and/or balance board respectively.

6. The method of claim 5, wherein the first phase OVI module vision therapy includes two levels and the third phase OVI module vision therapy includes four levels.

7. The method of claim 1, wherein performing one of the first or third phase DOMP module vision therapy comprises providing a plurality of targets on a display in response to running of a software product; establishing parameters of which targets of the plurality of targets the user is to locate and what order to locate the targets; locating a hand controlled remote indicator on the target on the display; shooting the target in response to depression of a trigger of a hand controlled remote; repeating the locating and shooting steps for each target established by the parameters until the user has shot once at each target; and sounding an auditory alert whether the target has or has not been shot in response to each instance a user shoots at a target.

8. The method of claim 7, further comprising providing feedback as to whether head and/or body motion is detected from a head sensor and/or balance board respectively.

9. The method of claim 8, wherein the first phase DOMP module vision therapy includes five levels and the third phase DOMP module vision therapy includes one level.

10. The method of claim 1, wherein performing one of the first or third phase VMI module vision therapy comprises providing a first target, a second target and a line connecting the first target and second target on a display in response to running of a software product; locating a hand controlled remote indicator on the first target on the display; locating a user's eyes on the first target in response to input from a head sensor; directing the hand controlled remote indicator along the line from the first target to the second target while synchronously following the hand controlled remote indicator along the line with user's eyes; and sounding an auditory alert in response to the eye/eyes and hand losing synchronization.

11. The method of claim 10, further comprising providing feedback as to whether head and/or body motion is detected from a head sensor and/or balance board respectively.

12. The method of claim 11, wherein the first phase VMI module vision therapy includes four levels and the third phase VMI module vision therapy includes one level.

13. The method of claim 1, wherein enhancing the stability of the visual input system comprises performing a first phase FA module vision therapy, the first phase FA module vision therapy having three levels.

14. The method of claim 9, wherein performing the first phase FA module vision therapy comprises randomly providing a plurality of marked targets and a plurality of unmarked targets on a display in response to running of a software product; locating one marked target of the plurality of marked targets; locating a hand controlled remote indicator on the one marked target on the display; shooting the target in response to depression of a trigger of a hand controlled remote; maintaining the hand controlled remote indicator steady on the one marked target for a predetermined period of time; and sounding an auditory alert in response to the hand controlled remote indicator moving off of the one marked target.

15. The method of claim 10, further comprising providing feedback as to whether head and/or body motion is detected from a head sensor and/or balance board respectively.

16. The method of claim 1, wherein developing speed of visual information processing and stability of visuomotor performance comprises performing a third phase FA module vision therapy, the third phase FA module vision therapy having two levels.

17. The method of claim 12, wherein performing the third phase FA module vision therapy comprises randomly providing a plurality of marked targets and a plurality of unmarked targets on a display in response to running of a software product; locating one marked target of the plurality of marked targets; locating a hand controlled remote indicator on the one marked target on the display; shooting the target in response to depression of a trigger of a hand controlled remote; maintaining the hand controlled remote indicator steady on the one marked target for a predetermined period of time; and sounding an auditory alert in response to the hand controlled remote indicator moving off of the one marked target.

18. The method of claim 13, further comprising providing feedback as to whether head and/or body motion is detected from a head sensor and/or balance board respectively.

19. The method of claim 1, further comprising scoring a performance of a user in each phase of the vision therapy.

20. A method of using a vision therapy system having a computer operating the system, a projector projecting visual graphics, a display for displaying the projection, and input devices for providing interaction by the user with the system, the method comprising:
  initiating first phase of a vision therapy of enhancing the stability of the visual input system, wherein enhancing the stability of the visual input system comprises performing a first phase VME module vision therapy, a first phase OVI module vision therapy, a first phase DOMP module vision therapy and a first phase VMI module vision therapy;
  initiating second phase of the vision therapy of developing fusional sustenance; and
  initiating third phase of the vision therapy of developing speed of visual information processing and stability of visuomotor performance, wherein the developing speed of visual information processing and stability of visuomotor performance comprises performing a third phase VME module vision therapy, a third phase OVI module vision therapy, a third phase DOMP module vision therapy and a third phase VMI module vision therapy.

* * * * *